(12) United States Patent
Zhang et al.

(10) Patent No.: US 6,951,935 B2
(45) Date of Patent: Oct. 4, 2005

(54) HETEROATOM-SUBSTITUTED PORPHYRINS AND METHODS FOR SYNTHESIS OF SAME

(75) Inventors: X. Peter Zhang, Knoxville, TN (US); Ying Chen, Knoxville, TN (US); Guangyao Gao, Knoxville, TN (US); Andrew J. Colvin, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 10/401,211

(22) Filed: Mar. 27, 2003

(65) Prior Publication Data

US 2003/0236400 A1 Dec. 25, 2003

Related U.S. Application Data

(60) Provisional application No. 60/368,295, filed on Mar. 28, 2002.

(51) Int. Cl.$^7$ .................... C07D 487/22; A61K 31/555; A61K 31/409
(52) U.S. Cl. ...................................... 540/145
(58) Field of Search ......................... 540/145

(56) References Cited

PUBLICATIONS

Gao, et al., Organic Letters, 2003, vol. 5, No. 18, 3261–3264.*
Johnson et al. {Journal of the Chemical Society [Section] C: Organic (1966), (8), 794–8}.*
Evans et al. {Tetrahedron, 33(6), (1977), 629–33}.*
Fuhrhop et al. {Journal of the American Chemical Society (1975), 97(24), 7141–52}.*
Callot et al. {Journal of the American Chemical Society (1978), 100(15), 4733–41}.*

* cited by examiner

*Primary Examiner*—Richard L. Raymond
*Assistant Examiner*—Kahsay Habte
(74) *Attorney, Agent, or Firm*—Jenkins Wilson and Taylor, P.A.

(57) ABSTRACT

Novel methods of synthesizing heteroatom-containing porphyrins and metalloporphyrins are disclosed. Novel heteroatom-containing porphyrin and metalloporphyrin compounds are also disclosed. The new methods advantageously utilize metal-catalyzed cross-coupling and amination reactions to produce porphyrin compounds useful in a variety of practical applications.

36 Claims, 8 Drawing Sheets

Ligand:

HETEROATOM-SUBSTITUTED PORPHYRINS AND METHODS FOR SYNTHESIS OF SAME

CROSS REFERENCE TO RELATED APPLICATIONS

This application claims the benefit of U.S. Provisional Application No. 60/368,295, filed Mar. 28, 2002, which application is incorporated herewith in its entirety.

TECHNICAL FIELD

The present invention relates to methods of synthesizing heteroatom-substituted porphyrins, and further relates to novel heteroatom-substituted porphyrins.

| Abbreviations | |
|---|---|
| Ac | acetyl |
| Bu | butyl |
| calc'd | calculated |
| dba | dibenzylidieneacetone |
| DPEphos | bis(2-diphenylphosphinophenyl) ether |
| DMSO | dimethyl sulfoxide |
| Et | ethyl |
| KOBut | potassium butoxide |
| Me | methyl |
| OTf | trifluoromethanesulfonate |
| Ph | phenyl |
| Pr | propyl |
| rt | room temperature |
| TFA | trifluoroacetate |
| THF | tetrahydrofuran |
| TLC | thin layer chromatography |
| vis | visible |

BACKGROUND ART

Synthetic porphyrins and metalloporphyrins have become increasingly important in numerous and diverse technical fields. Their several practical applications include their use as sensitizers in photodynamic therapy (PDT) (Mody, (2000) *J. Porphyrins Phthalocyanines* 4: 362); in electron transfer (Lippard and Berg, (1994) *Principles of Bioinorganic Chemistry*, University Science Book: Mill Valley, Calif.); in DNA strand cleavage (Bennett et al., (2000) *Proc. Natl. Acad. Sci.* 97: 9476; Hashimoto et al., (1983) *Tetrahedron letters*, 24: 1523); as carriers of cytotoxic anticancer drugs such as platinum (Song et al., (2002) *Inorganic Biochemistry* 83: 83; and Lottner et al. (2002) *J. Med. Chem.*, 45, 2064); as components of synthetic receptors (Jain and Hamilton, (2002) *Org. Lett.* 2: 1721); and as oxidation catalysts (Guo et al. (2001) *J. Mol. Catal. A Chem.* 170: 43). Additionally, functionalized porphyrins have become important leads in current drug discovery techniques (See Mody, supra, and Priola et al., (2002) *Science* 287: 1503). Accordingly, the development of new methodologies and strategies to improve the synthesis of functionalized porphyrins has become highly desirable.

Numerous methods for the synthesis of porphyrins are known. The classical methods for porphyrin synthesis typically require harsh reaction conditions and can provide disappointingly low yields (Rothemund, (1935) *J. Am. Chem. Soc.*, 57: 2010; Adler et al., (1967) *J. Org. Chem.* 32: 476). Newer methodologies, such as those developed by Lindsey and colleagues, have resolved certain issues regarding reaction conditions and yields (Lindsey et al., (1987) *J. Org. Chem.* 52: 827). More recently, transition metal-catalyzed organic synthesis methodologies (e.g., Suzuki coupling and Heck-type coupling), have been successfully employed with porphyrin systems, providing versatile and general synthetic approaches for the preparation of a variety of functionalized porphyrins and porphyrin analogs. See, e.g., DiMagno et al., (1993) *J. Org. Chem.*, 58: 5983; DiMagno, et al. (1993) *J. Org. Chem.* 115: 2513; Chan, et al., (1995) *Tetrahedron* 51: 3129; Zhou et al., (1996) *J. Org. Chem.* 61: 3590; Risch and Rainer, (1997) *Tetrahedron Letters* 38: 223; Hyslop et al., (1998) *Am. Chem. Soc.* 120: 12676; Boyle and Shi, (2002) *J. Chem. Soc. Pekin Trans.*, 1: 1397; and Pereira, et al., (2002) *J. Chem. Soc. Pekin Trans.*, 2: 1583. See also, Suzuki, (1998) *Metal-Catalyzed Cross-Coupling Reactions*, pp. 49–97, Wiley-VCH, Weinheim, Germany; U.S. Pat. No. 5,550,236 and U.S. Pat. No. 5,756,804, which references are incorporated herein by reference.

However, each of these foregoing methods possesses undesirable aspects that should be mitigated, including incompatibilities between catalysts and reaction compounds, low turnover number (TON) and low turnover frequency (TOF). Thus, despite recent advances in porphyrin chemistry, a need still exists for facile and general syntheses for, in particular, heteroatom-substituted porphyrins and metalloporphyrins.

SUMMARY OF THE INVENTION

Novel heteroatom-substituted porphyrin compounds are one aspect of the present invention. Novel compounds of the present invention have the structure of Formula I, as follows:

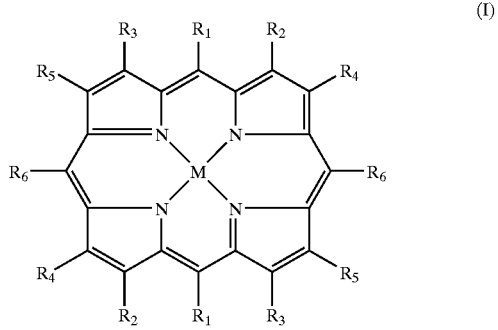

(I)

In Formula I, M is $H_2$ or a transition metal; each $R_1$, $R_2$, $R_3$, $R_4$, $R_5$ and $R_6$ are each independently selected from the group consisting of Y, H, alkyl, substituted alkyl, arylalkyl, aryl, and substituted aryl; Y is a heteroatom-containing moiety; and at least one of $R_1$, $R_2$, $R_3$, $R_4$, $R_5$ and $R_6$ is Y. In one preferred embodiment of the invention, M is selected from the group consisting of $H_2$, Fe, Zn and Ni, although numerous other transition metals are useful in the invention. In one embodiment of the invention, Y is a heteroatom-containing moiety selected from the group consisting of $NR_7R_8$, $NR_{10}$, $OR_{10}$, $PR_7R_8$, $SR_{10}$, $SiR_7R_8R_9$, $BR_7R_8$, $GeR_7R_8R_9$, $SnR_7R_8R_9$ and $SeR_{10}$, wherein $R_7$, $R_8$, $R_9$, and $R_{10}$ are each independently selected from the group consisting of H, alkyl, substituted alkyl, arylalkyl, aryl, and substituted aryl. In another embodiment of the invention, Y is a selected from the group consisting of amino, substituted amino, imino, substituted imino, and phenoxy groups.

Another aspect of the present invention is a method of synthesizing a heteroatom-substituted porphyrin compound, whereby a porphyrin precursor and a heteroatom reagent is reacted in the presence of a ligand, a metal compound, and a base in order to yield the substituted porphyrin. In one embodiment of the invention, the porphyrin precursor has the same general structure of Formula I, wherein M is $H_2$ or a transition metal; each $R_1$, $R_2$, $R_3$, $R_4$, $R_5$ and $R_6$ are each independently selected from the group consisting of X, H, alkyl, substituted alkyls, arylalkyls, aryls, and substituted aryls, and X is selected from the group consisting of halogen, trifluoromethanesulfonate (OTf), haloaryl and haloalkyl. In this embodiment of the invention, at least one of $R_1$, $R_2$, $R_3$, $R_4$, $R_5$ and $R_6$ is X. In a preferred embodiment, M is selected from the group consisting of $H_2$, Zn, Fe and Ni. Preferred heteroatom reagents comprise moieties in which the heteroatom is selected from the group consisting of N, O, P, S, Si, B, Ge, Sn, and Se, with N and O being particularly preferred.

Accordingly, it is an object of the present invention to provide a novel heteroatom-substituted porphyrin compound and a novel method of synthesizing a heteroatom-substituted porphyrin compound. This object is achieved in whole or in part by the present invention.

Some of the objects and aspects of the invention having been stated herein above, other objects will be evident as the description proceeds, when taken in connection with the accompanying examples, drawings, and descriptions set forth hereinbelow.

BRIEF DESCRIPTION OF THE DRAWINGS

In FIG. 1, "M" represents $H_2$, or a transition metal; "X" represents a reactive group such as, for example a halide, trifluoromethanesulfonate (OTf), haloalkyl or haloaryl; and "Y" is heteroatom moiety such as, for example, $NR_7R_8$, $NR_{10}$, $OR_{10}$, $PR_7R_8$, $SR_{10}$, $SiR_7R_8R_9$, $BR_7R_8$, $GeR_7R_8R_9$, $SnR_7R_8R_9$ and $SeR_{10}$, where $R_7$, $R_8$, $R_9$, and $R_{10}$ are each independently, for example, H, alkyl, substituted alkyl, arylalkyl, aryl, or substituted aryl.

FIG. 3A shows two generalized schemes of palladium-catalyzed amination reactions of meso-monobromoporphyrins (left-hand scheme) and meso-dibromoporphyrins (right-hand scheme). FIG. 3B shows the same two amination reactions with specific reaction components and conditions indicated. In FIG. 3B, the upper reaction scheme represents the amination of a meso-monobromoporphyrin, while the lower scheme represents the amination of a meso-dibromoporphyrin.

FIG. 5A is a general scheme of the synthesis of aminophenylporphyrins by a palladium-catalyzed amination reaction of p-bromophenyl porphyrin and its zinc complex. FIG. 5B illustrates a particular embodiment of the general scheme of FIG. 5A, wherein specific reaction conditions and components are indicated. FIG. 5C illustrates yet another particular embodiment of the general reaction shown in FIG. 5A, wherein specific reaction conditions and components are indicated. FIG. 5D illustrates a generalized scheme of a palladium-catalyzed reaction of a tetrakis-p-bromophenyl porphyrin that yields a tetrakis-aminophenyl porphyrin.

DETAILED DESCRIPTION OF THE INVENTION

Figure 1:
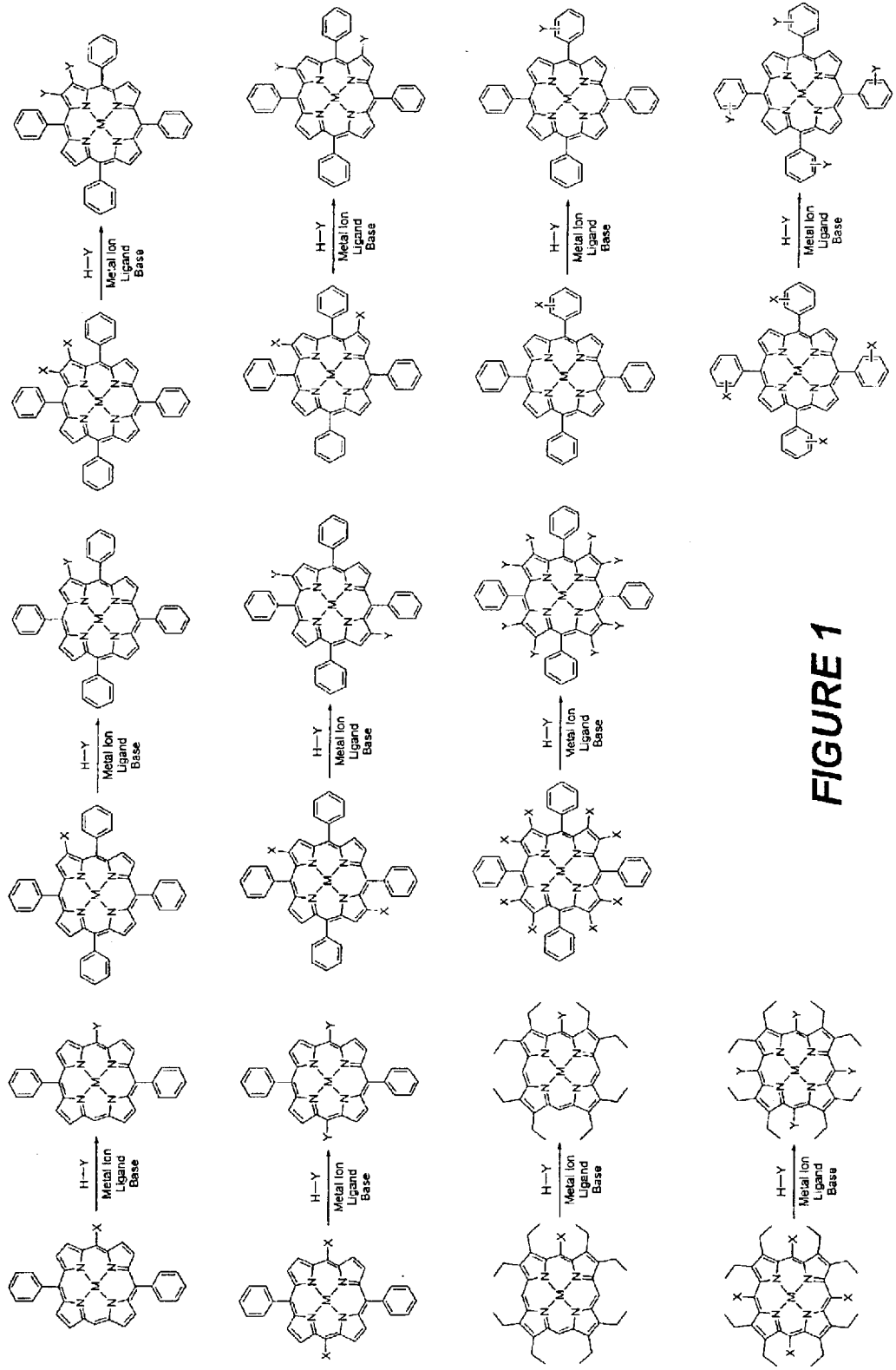
FIG. 1 illustrates several schemes by which heteroatom substituents (e.g., nitrogen, oxygen, etc.) may be substituted into porphyrins by metal/ligand-catalyzed cross-coupling or amination reactions.

Throughout the specification and claims, a given chemical formula or name shall encompass all stereoisomers.

The term "independently selected" is used herein to indicate that the R groups, e.g., $R_1$, $R_2$, $R_3$ or $R_4$, can be identical or different (e.g., $R_1$, $R_2$ and $R_3$ may all be substituted alkyls, or $R_1$ and $R_4$ may be a substituted alkyl and $R_3$ may be an aryl, etc.). Moreover, "independently selected" means that in a multiplicity of R groups with the same name, each group may be identical to or different from each other (e.g., one $R_1$ may be an alkyl, while another $R_1$ group in the same compound may be aryl; one $R_2$ group may be H, while another $R_2$ group in the same compound may be alkyl, etc.).

A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

As used herein, the term "alkyl" means $C_{1-20}$ inclusive, linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups.

The alkyl group can be optionally substituted with one or more alkyl group substituents which can be the same or different, where "alkyl group substituent" includes alkyl, halo, arylamino, acyl, hydroxy, aryloxy, alkoxyl, alkylthio, arylthio, aralkyloxy, aralkylthio, carboxy, alkoxycarbonyl, oxo and cycloalkyl. Suitable substituted alkyls include, for example, benzyl, trifluoromethyl and the like. There can be optionally inserted along the alkyl chain one or more oxygen, sulfur or substituted or unsubstituted nitrogen atoms, wherein the nitrogen substituent is hydrogen, alkyl (also referred to herein as "alkylaminoalkyl"), or aryl. "Branched" refers to an alkyl group in which an alkyl group, such as methyl, ethyl or propyl, is attached to a linear alkyl chain.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, the term "aryl" means a cyclic aromatic comprising about 5 to about 10 carbon atoms, including 5 and 6-membered hydrocarbon and heterocyclic aromatic rings.

The aryl group can be optionally substituted with one or more aryl group substituents which can be the same or different, where "aryl group substituent" includes alkyl, aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NR'R", where R' and R" can be each independently hydrogen, alkyl, aryl and aralkyl.

Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like.

The term "alkoxy" is used herein to refer to the —$OZ_1$ radical, where $Z_1$ is selected from the group consisting of alkyl, substituted alkyl, cycloalkyl, substituted cycloalkyl, heterocycloalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z_1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

The term "amino" is used herein to refer to the group —$NZ_1Z_2$, where each of $Z_1$ and $Z_2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof. Additionally, the amino group may be represented as $N^+Z_1Z_2Z_3$, with the previous definitions applying and $Z_3$ being either H or alkyl.

A "heteroatom," as used herein, is an atom other than carbon. Preferred heteroatoms are heteroatoms selected from the group consisting of N, O, P, S, Si, B, Ge, Sn, and Se. In the present invention, the heteroatoms N and O are particularly preferred. "Halide" or "halo" is defined as being selected from the group consisting of Br, Cl, I and F. In the present invention, the halo groups Br and I are particularly preferred.

Heteroatom-substituted porphyrins of the present invention are synthesized by reacting a porphyrin precursor and a heteroatom reagent in the presence of a metal compound, ligand and a base. Although applicants do not wish to be bound to any particular theory of the invention, it appears that the metal and ligand together (e.g., as a metal-ligand complex, or metal/ligand composition) function as a catalyst for the reaction, by which a heteroatom-substituted porphyrin is produced.

Depending on the heteroatom reagent, reactions of the present invention may be, for example, cross-coupling reactions, amination reactions, or arylamination reactions. For example, in one embodiment, the metal compound and ligand together (in the configuration of a metal complex) catalyze the cross coupling reaction between the porphyrin precursor and the heteroatom reagent to yield the heteroatom-substituted porphyrin. Representative methods of the present invention are generally illustrated in the several schemes shown in FIG. 1.

Porphyrin precursors of the present invention have the structure of Formula I:

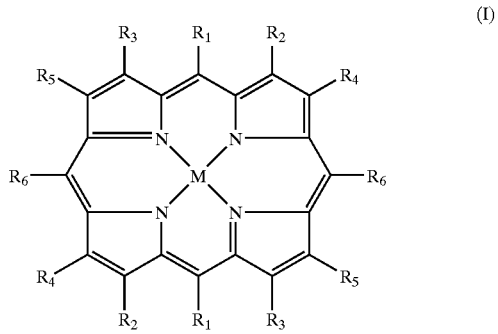

(I)

wherein:
M is $H_2$ or a transitional metal;
each $R_1$, $R_2$, $R_3$, $R_4$, $R_5$ and $R_6$ are each independently selected from the group consisting of X, H, alkyl, substituted alkyls, arylalkyls, aryls and substituted aryls;
X is selected from the group consisting of halogen, trifluoromethanesulfonate (OTf), haloaryl and haloalkyl, and at least one of $R_1$, $R_2$, $R_3$, $R_4$, $R_5$ and $R_6$ is X.

Transitional metals of the present invention include any of the 30 metals in the 3d, 4d and 5d transition metal series of the Periodic Table of the Elements, including the 3d series that includes Sc, Ti, V, Cr, Mn, Fe, Co, Ni, Cu, and Zn; the 4d series that includes Y, Zr, Nb, Mo, Tc, Ru, Rh, Pd, Ag and Cd; and the 5d series that includes Lu, Hf, Ta, W, Re, Os, Ir, Pt, Au and Hg. In a preferred embodiment, M is $H_2$ or a transition metal from the 3d series. In a particularly preferred embodiment, M is selected from the group consisting of $H_2$, Zn, Fe, and Ni. In an even more preferred embodiment, M is selected from the group consisting of $H_2$ and Zn.

In a preferred embodiment, the porphyrin precursor compound is halogenated, that is, at least one of $R_1$, $R_2$, $R_3$, $R_4$, $R_5$ and $R_6$ is halogen. In a more preferred embodiment, at least one meso-position of the porphyrin precursor compound is halogenated. In another preferred embodiment, more than one meso-position of the porphyrin precursor compound is halogenated. When a porphyrin precursor compound of the present invention is halogenated, one preferred halogen group is Br, although other halogen groups are also useful in the practice of the invention.

In a preferred embodiment of the invention, the heteroatom reagent has the chemical structure Y—H, where Y is heteroatom-containing moiety comprising at least one of N, O, P, S, Si, B, Ge, Sn, and Se. Exemplary heteroatom-containing moieties include, but are not limited to, $NR_7R_8$, $NR_{10}$, $OR_{10}$, $PR_7R_8$, $SR_{10}$, $SiR_7R_8R_9$, $BR_7R_8$, $GeR_7R_8R_9$, $SnR_7R_8R_9$ and $SeR_{10}$, wherein $R_7$, $R_8$, $R_9$, and $R_{10}$ are each independently selected from the group consisting of H, alkyl, substituted alkyl, arylalkyl, aryl, and substituted aryl. In a preferred embodiment, the heteroatom-containing moiety comprises one of N or O.

In one preferred embodiment, the heteroatom reagent comprises at least one amino group. Suitable amino groups include, but are not limited to, primary amines, secondary amines, anilines, substituted aniline derivatives, aromatic amines, primary aliphatic amines, secondary aliphatic amines and cycloaliphatic amines. Specific amino groups useful in the present invention include, but are not limited to, aniline, 4-nitroaniline, N-methylaniline, 4-trifluoromethylaniline, p-anisidine, 3,5-di-tert-butylaniline, n-hexylamine, benzylamine, diphenylamine, n-butylamine, 4-aminomethylpyridine, and o-toluidine. In an alternative preferred embodiment, the heteroatom reagent comprises an imino group. Suitable imino groups include but are not limited to benzophenone imino groups.

In yet another preferred embodiment, the heteroatom reagent comprises an aryl or aryl halide group, which groups are sometimes referred to herein as phenol or substituted phenol groups. Suitable aryl groups include phenol, 4-methoxyphenol, 4-t-butylphenol, 4-fluorophenol, 2-isopropylphenol, 3-cresol, 4-cresol, and 4-methoxyphenol.

Reactions of the present invention involve a catalyst, which catalyst generally has the form of a metal complex. The metal complex comprises a metal compound of the present invention complexed with a ligand, preferably a phosphine ligand, of the present invention. Metal compounds of the present invention may optionally be provided as metal precursors. Thus, as used herein, a "metal compound" may also be referred to as a "metal precursor," a "metal precursor compound," a "metal salt," or a "metal ion."

The metal precursor compounds may be characterized by the general formula $M'(L)_n$ (also referred to as $M'L_n$ or $M'—L_n$) where $M'$ is a metal selected from the group consisting of Groups 5, 6, 7, 8, 9 and 10 of the Periodic Table of Elements, L is independently each occurrence, a neutral or charged ligand, and n is a number 0, 1, 2, 3, 4, or 5, depending on $M'$. In more specific embodiments, $M'$ is selected from the group consisting of Ni, Pd, Fe, Pt, Ru, Rh, Co and Ir. In preferred embodiments, $M'$ is selected from the group consisting of Pd, Ni, Cu or Pt; in a more preferred embodiment, $M'$ is Pd. L is a compound chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is charged, L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When L is neutral, L may be selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino.

Specific examples of suitable metal precursor compounds include $Pd(dba)_2$, $Pd_2(dba)_3$, $Pd(OAc)_2$, $PdCl_2$, $Pd(TFA)_2$, $(CH_3CN)_2PdCl_2$, and the like. Particularly preferred metal precursor compounds of the present invention include $Pd(OAc)_2$ and $Pd_2(dba)_3$, where "Ac" means acetyl and. "dba" means dibenzylidieneacetone.

In the practice of the present invention, ligands of the invention may be combined with such a metal compound in order to provide a catalyst for the heteroatom-substitution reaction. For example, the ligand may be added to a reaction vessel at the same time as metal precursor compound along with the reactants. In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst.

Figure 2:
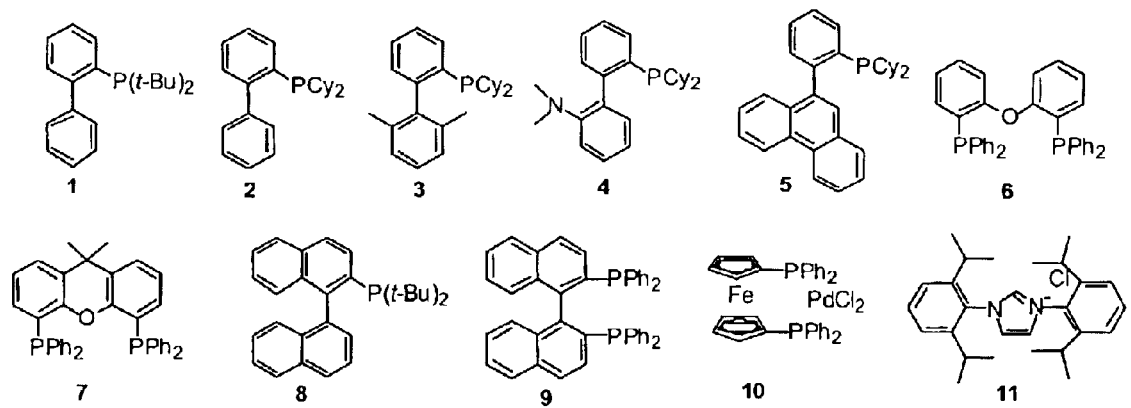
FIG. 2 illustrates the chemical structures of eleven compounds that are representative, although not inclusive, of phosphine ligands useful in the present invention.

Generally, the ligands useful in this invention may be purchased or prepared by methods known to those of skill in the art. The ligand is preferably a phosphine ligand. Suitable phosphine ligand-metal complexes are disclosed in U.S. Pat. No. 6,268,513 to Guram et al., which patent is incorporated herein. Phosphine ligands may comprise dicycloalkylphenyl phosphine ligand or dialkylphenyl phosphine ligand, which may be in the form of a metal-ligand complex or a metal precursor/ligand composition. In an alternative embodiment, the phosphine ligands useful in this invention comprises a cyclopentadienyl ring. Specific ligands that are useful in the practice of the present invention include, but are not limited to, those whose structures are shown in FIG. 2. Particularly preferred ligands include DPEphos (FIG. 2, Ligand 6), BINAP (FIG. 2, Ligand 9) and 2-(Di-t-butylphosphino)-1, 1-binaphthyl (FIG. 2, Ligand 8).

To carry out the process of this invention for one type of reaction, the porphyrin precursor, the heteroatom reagent, a base, a catalytic amount of metal precursor compound and a catalytic amount of the ligand are added to an inert solvent or inert solvent mixture. In a batch methodology, this mixture is stirred at a temperature of from 0° C. to 200° C., preferably at from 30° C. to 170° C., particularly preferably at from 50° C. to 150° C., and more particularly preferably at from 60° C. to 120° C., with 68° C. being most particularly preferred. The mixture is stirred for a period of from 5 minutes to 100 hours, preferably from 15 minutes to 70 hours, particularly preferably from ½ hour to 50 hours, most particularly preferably from 1 hour to 30 hours. After the reaction is complete, the catalyst may be obtained as solid and separated off by filtration. The crude product is freed of the solvent or the solvents and is subsequently purified by methods known to those skilled in the art and matched to the respective product, e.g. by recrystallization, distillation, sublimation, zone melting, melt crystallization or chromatography.

Solvents suitable for the process of the invention are, for example, ethers (e.g., diethyl ether, dimethoxymethane, diethylene glycol, dimethyl ether, tetrahydrofuran (THF), dioxane, diisopropyl ether, tert-butyl methyl ether), hydrocarbons (e.g., hexane, iso-hexane, heptane, cyclohexane, benzene, toluene, xylene), alcohols (e.g., methanol, ethanol, 1-propanol, 2-propanol, ethylene glycol, 1-butanol, 2-butanol, tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), water and mixtures thereof. Particularly preferred solvents are ethers (e.g., dimethoxyethane, THF), and hydrocarbons (e.g., cyclohexane, benzene, toluene, xylene). Most particularly preferred are toluene and THF.

Bases which are useful in the process of the invention are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, alkali metal and alkaline earth metal phosphates, primary, secondary and tertiary amines, alkali metal and alkaline earth fluorides, and ammonium fluorides. Preferred bases include but are not limited to n-BuLi, LDA, $NaNH_2$, NaOH, $Et_3N$, NaOAc, KOt-Bu, NaOt-Bu, $Cs_2CO_3$, $K_2CO_3$, $K_3PO_4$, carbonate-containing compounds, and phosphate-containing compounds. Particularly preferred bases include, but are not limited to, $Cs_2CO_3$ and NaOt-Bu. The base is preferably used in the process of the invention in an amount of from about 0.1 to about 100 equivalents, particularly preferably from about 0.5 to about 50 equivalents, very particularly preferably from about 1.0 to about 10 equivalents, and most particularly from about 1.0 to about 1.5 equivalents.

The metal precursor compound used in this reaction is as described above and may be added to the process along with the other reactants. The metal portion of the catalyst (i.e., the metal precursor compound) is used in the process of this invention in a proportion of from about 0.01 to about 100 mol %, preferably from about 0.1 to about 50 mol %, particularly preferably from about 0.5 to about 10 mol %, and most particularly preferably from about 1 to about 5 mol %. The ligand component of the catalyst, which may or may not be complexed to the metal precursor compound, is used in the reaction in a proportion of from about 0.01 to about 100 mol %, preferably from 0.1 to about 50 mol %, particularly preferably from about 0.5 to about 10 mol %, and most particularly preferably from about 1 to about 5 mol %. These amounts may be combined to give metal precursor to ligand ratios useful in the process. It is also possible, if desired, to use mixtures of two or more different ligands.

Figure 3A:
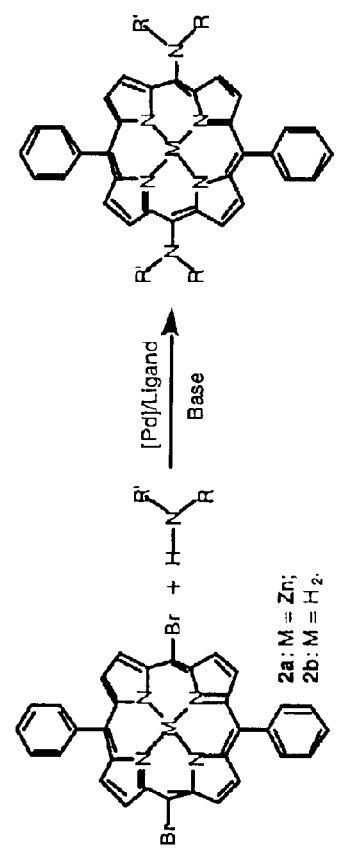
FIGS. 3A and 3B are schemes of particular embodiments of the present invention.
Figure 3A:
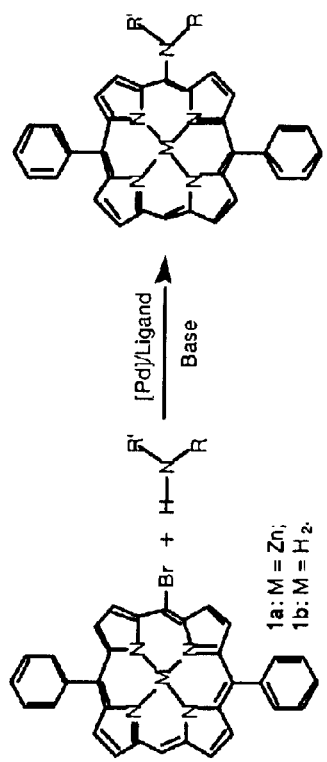
Figure 3B:
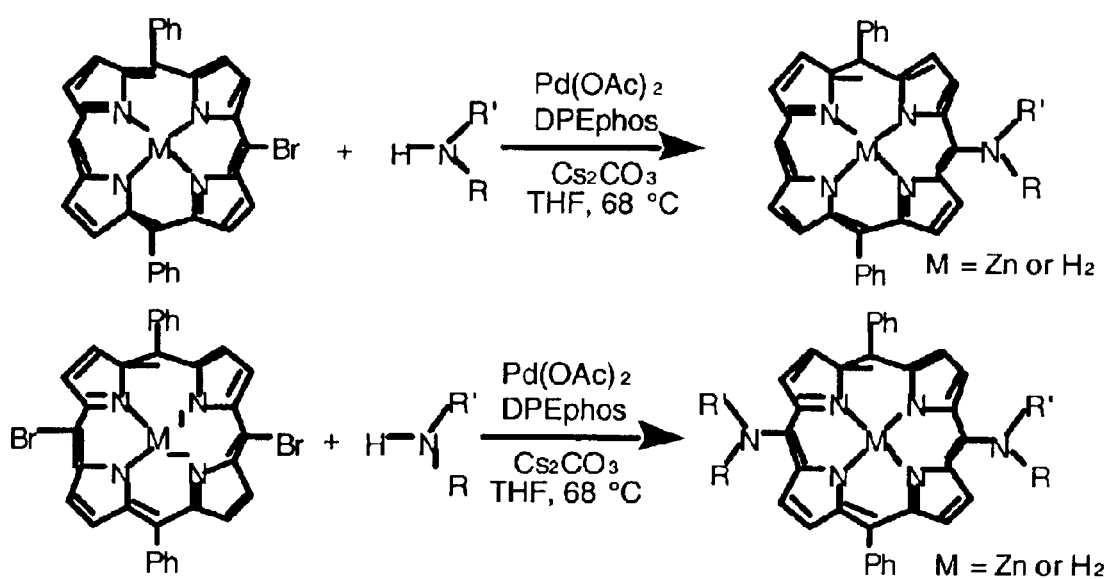

In preferred embodiments of the invention, at least one meso-position of the synthesized heteroatom-substituted porphyrin is substituted; that is, the heteroatom-substituted porphyrin is a meso-substituted porphyrin. In one embodiment of the invention, amino-substituted porphyrins are obtained from halogenated porphyrin precursors via palladium-catalyzed amination. Specifically, meso-arylamino- and alkylamino-substituted porphyrins are efficiently synthesized by reacting meso-halogenated porphyrins with amines via palladium-catalyzed amination. A general schematic of this embodiment is illustrated in FIG. 3A. FIG. 3B illustrates two particular embodiments of the invention. In the schematic on the left side of the figure, the porphyrin precursors 5-bromo-10,20-diphenylporphyrine and its corresponding zinc complex [5-bromo-10,20-diphenyl porphyrino]zinc(II) are each reacted with an amino group to yield the illustrated amino-substituted porphyrin. In the schematic on the right side of the picture, [5,15-dibromo-10,20-diphenylporphyrino]zinc(II) and its corresponding zinc complex [5,15-dibromo-10,20-diphenylporphyrino] zinc(II) are each reacted with an amino group to provide the indicated amino-substituted porphyrin. The precursors and amine reagents are reacted in the presence of palladium acetate and the commercially available phosphine ligand bis(2-diphenylphosphinophenyl) ether, or "DPEphos".

Figure 4:
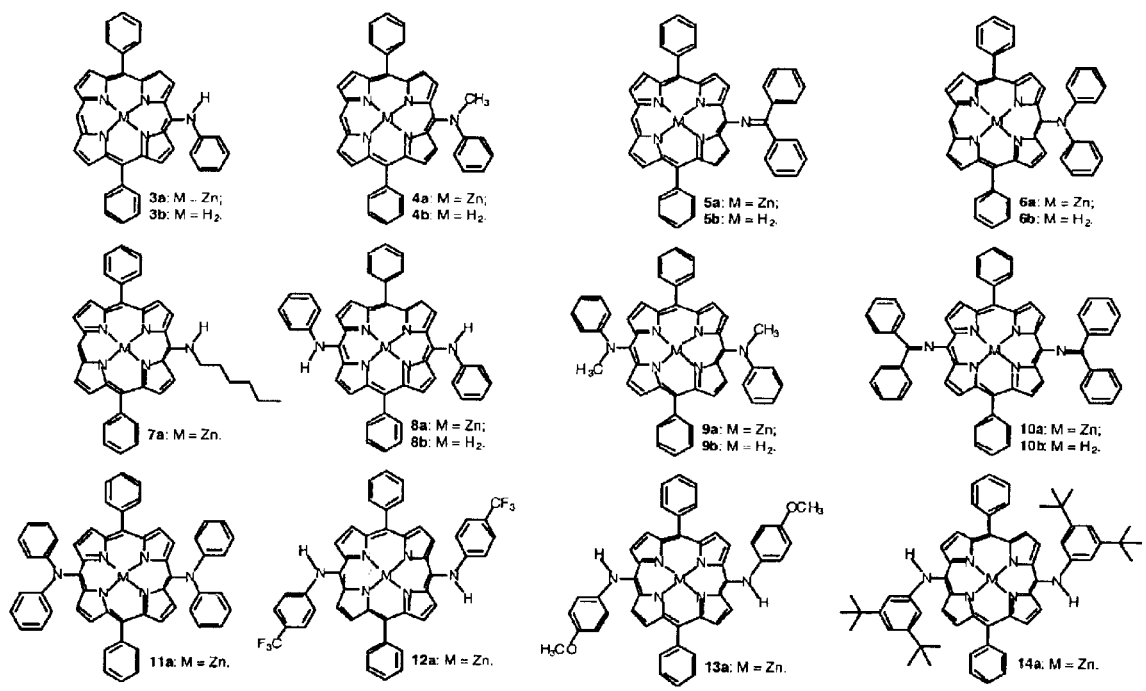
FIG. 4 illustrates the chemical structures of several compounds of the present invention, which compounds are synthesized by methods of the present invention. The compound numbers shown in FIG. 4 (e.g., 3a, 3b, 4a, 4b, etc.) correspond to the compound numbers indicated in Table 1, below.
Figure 5A:
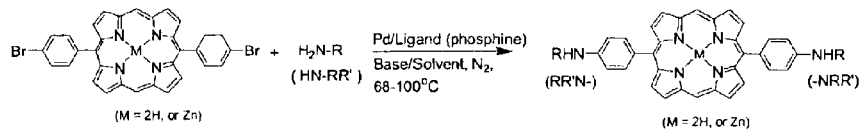
FIGS. 5A–5D are schemes of particular embodiments of the present invention.
Figure 5B:
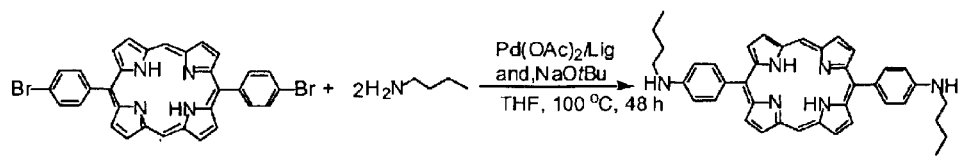
Figure 5C:
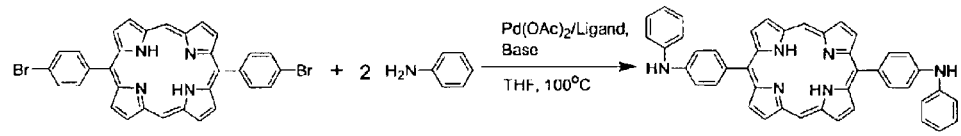
Figure 5D:
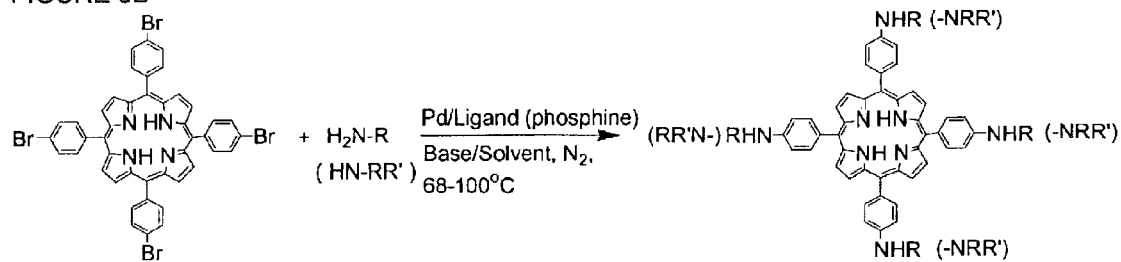

In other embodiments of the invention, a variety of different amines are efficiently coupled with the meso-brominated 10,20-diphenylporphyrins 5-bromo-10,20-diphenylporphyrine and 5,15-dibromo-10,20-diphenylporphyrine (compounds 1b and 2b in Table 1) as well as their corresponding zinc complexes [5-bromo-10, 20-diphenylporphyrino]zinc(II) and [5,15-dibromo-10,20-diphenylporphyrino]zinc(II) (compounds 1a and 2a in Table 1). The meso-arylamino- and alkylamino-substituted porphyrins that are obtained are summarized in Table 1, below, with the structures of the resulting compound being shown in FIG. 4. Specifically, both the primary aniline (Table 1, entry 1) and the secondary N-methylaniline (Table 1, entry 3) can be effectively coupled with 1a to give monoamino-substituted porphyrins 3a and 4a, respectively. When 2a is used, the corresponding diamino-substituted porphyrins 8a (Table 1, entry 10) and 9a (Table 1, entry 12) are synthesized via double amination reactions. Substituted aniline derivatives such as 4-trifluoromethylaniline (Table 1, entry 17), p-anisidine (Table 1, entry 18) and 3,5-di-tert-butylaniline (Table 1, entry 19) also give high yields of double amination products when reacted with 2a. Primary aliphatic amines can also be well-coupled, as demonstrated in the case of n-hexylamine with 1a (Table 1, entry 9).

In addition to primary and secondary amines, imines are also suitable coupling partners under similar reaction conditions. When benzophenone imine was employed, monoimino-substituted porphyrin 5a (Table 1, entry 5) and diimino-substituted porphyrin 10a (Table 1, entry 14) are obtained from its reactions with 1a and 2a, respectively.

TABLE 1

Palladium-Catalyzed Amination of meso-bromoporphyrins with amines

| entry | reactant[b] | amine | time (h)[c] | product[d] | yield (%)[e] |
|---|---|---|---|---|---|
| 1 | 1a | $PhNH_2$ | 13 | 3a | 95 |
| 2 | 1b | $PhNH_2$ | 19 | 3b | 98 |
| 3 | 1a | Ph(Me)NH | 13 | 4a | 99 |
| 4 | 1b | Ph(Me)NH | 16 | 4b | 94 |
| 5 | 1a | $Ph_2$ C = NH | 22 | 5a | 94 |
| 6 | 1b | $Ph_2$ C = NH | 24 | 5b | 84 |
| 7 | 1a | $Ph_2NH$ | 25 | 6a | 61[f] |
| 8 | 1b | $Ph_2NH$ | 40 | 6b | 66 |
| 9 | 1a | $n-HexNH_2$ | 50 | 7a | 80 |
| 10 | 2a | $PhNH_2$ | 13 | 8a | 82 |
| 11 | 2b | $PhNH_2$ | 20 | 8b | 65 |
| 12 | 2a | Ph(Me)NH | 17 | 9a | 82 |
| 13 | 2b | Ph(Me)NH | 15 | 9b | 71 |
| 14 | 2a | $Ph_2$ C = NH | 16 | 10a | 84 |
| 15 | 2b | $Ph_2$ C = NH | 15 | 10b | 95 |
| 16 | 2a | $Ph_2NH$ | 50 | 11a | 30 |
| 17 | 2a | $(4-CF_3Ph)NH_2$ | 17 | 12a | 90 |
| 18 | 2a | $(4-CH_3OPh)NH_2$ | 16 | 13a | 94 |
| 19 | 2a | $(3,5-di-t-BUPh) NH_2$ | 62 | 14a | 95 |

Reactions were carried out at 68° C. in THF under $N_2$ with 1.0 equiv of bromoporphyrin, 3.6 equiv of amine for 1b and 2b or 4.8 equiv of amine for 1a and 2a, 5 mol % $Pd(OAc)_2$ and 7.5 mol % DPEphos in the presence of 1.4 equiv of $Cs_2CO_3$ per Br. Concentration: 0.05 mmol bromoporphyrin/5 mL THF. Yields represent isolated yields of > 95% purity as determined by $^1H$ NMR. The reaction was conducted using 10 mol % $Pd(OAc)_2$ and 15 mol % DPEphos in the presence of 2.8 equiv of NaOt-Bu.

In another embodiment of the invention, the methods of the present invention are carried out to produce aminophenylporphyrins. In one such embodiment, the porphyrin precursors are p-bromophenyl porphyrin and its zinc complex, and the amination reaction is catalyzed by palladium. Schemes for this reaction are illustrated in FIGS. 5A–5D, with exemplary aminophenylporphyrins obtained in this invention being described in Tables 2 and 3, below.

TABLE 2

5,15-di-aminophenylporphyrin and zinc complex synthesized via Pd catalyzed amination reaction

| Entry | Amine (8.0 equiv) | Ligand (10%) equiv | Base (8.0) equiv | Solvent | Time | Isolated yield (%) A M = 2H | B M = Zn (II) |
|---|---|---|---|---|---|---|---|
| 1 | 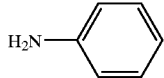 | 9 | Cs₂CO₃ | Toluene | 48 h | 70 | 66 |
|  |  | 9 | NaOtBu | Toluene | 48 h | 88 | — |
|  |  | 9 | NaOtBu | THF | 24 h | 95 | — |
|  |  | 9 | NaOtBu | THF | 13 h | 83 | — |
|  |  | 9 | Cs₂CO₃ | THF | 48 h | 92 | — |
|  |  | 9 | Cs₂CO₃ | THF | 48 h | 85ᵃ | — |
|  |  | 9 | NaOtBu | THF | 48 h | 92 | — |
|  |  | 9 | NaOtBu | THF | 48 h | — | — |
| 2 | 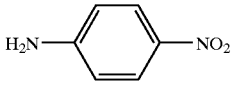 | 9 | Cs₂CO₃ | Toluene | 48 h | 76 | — |
| 3 |  | 3 | NaOtBu | THF | 48 h | 93 | 68 |
| 4 | 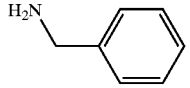 | 3 | NaOtBu | THF | 48 h | — | 83 |
| 5 | 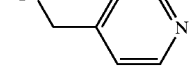 | 9 | NaOtBu | THF | 48 h | 88 | — |
|  |  | 8 | NaOtBu | THF | 48 h | 80 | — |
|  |  | 9 | Cs₂CO₃ | Toluene | 66.5 h | 45 | — |
| 6 | 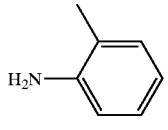 | 3 | NaOtBu | THF | 48 h | 87 | 73 |
| 7 | 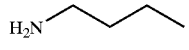 | 8 | NaOtBu | THF | 48 h | 83 | 93 |
|  |  | 8 | NaOtBu | THF | 24 h | 63 | — |
|  |  | 8 | NaOtBu | THF | 13 h | 76 | — |
|  |  | 8 | NaOtBu | THF | 48 h | 69ᵃ | — |
|  |  | 1 | Cs₂CO₃ | THF | 48 h | 79 | — |
|  |  | 2 | NaOtBu | THF | 48 h | 66ᵇ | — |
|  |  | 2 | NaOtBu | THF | 48 h | 99 | — |
|  |  | 3 | NaOtBu | THF | 48 h | 92 | — |
|  |  | 3 | NaOtBu | THF | 48 h | 93 | — |
| 8 | 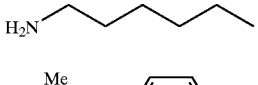 | 3 | NaOtBu | THF | 48 h | 90 | 53ᶜ |
| 9 | 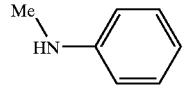 | 3 | NaOtBu | THF | 48 h | 88 | 73 |
| 10 | 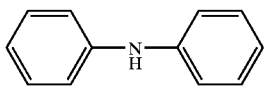 | 3 | NaOtBu | THF | 48 h | 81 | 57 |
|  |  | 9 | NaOtBu | THF | 48 h | 57 | — |

TABLE 2-continued 5,15-di-aminophenylporphyrin and zinc complex
synthesized via Pd catalyzed amination reaction

| Entry | Amine (8.0 equiv) | Ligand (10%) equiv | Base (8.0) equiv | Solvent | Time | Isolated yield (%) A M = 2H | B M = Zn (II) |
|---|---|---|---|---|---|---|---|
| 11 | Ph₂C=NH (diphenylmethanimine) | 1 | NaOtBu | THF | 48 h | 52 | — |
| 12 | morpholine (HN-O) | 8 | Cs₂CO₃ | THF | 48 h | 76 | — |
|    |                    | 8 | NaOtBu | THF | 48 h | 79 | — |

Note:
ᵃ, 4.0 equiv aniline; ᵇ, Pd(OAc)₂/Ligand = 10%/20%, ᶜ, ligand 7

TABLE 3

Tetrakis-aminophenylporphyrins synthesized from
tetrakis-p-bromophenylporphyrin through
Pd catalyzed amination reaction

| Entry | Amine 16.0 equiv | Pd (5%) equiv | Ligand (10%) equiv | Base (16.0) Solvent | °C. | Time | Isolated yield |
|---|---|---|---|---|---|---|---|
| 1 | H₂N-Ph (aniline) | Pd(OAc)₂ | 9 | NaOtBu THF | 100 | 72 h | 91% |
| 2 | H₂N-nBu (n-butylamine) | Pd(OAc)₂ | 8 | NaOtBu THF | 100 | 72 h | 86% |
| 3 | MeHN-Ph (N-methylaniline) | Pd(OAc)₂ | 9 | NaOtBu THF | 100 | 72 h | 82% |
| 4 | Ph-NH-Ph (diphenylamine) | Pd(OAc)₂ | 9 | NaOtBu THF | 100 | 72 h | 81% |

Figure 6:
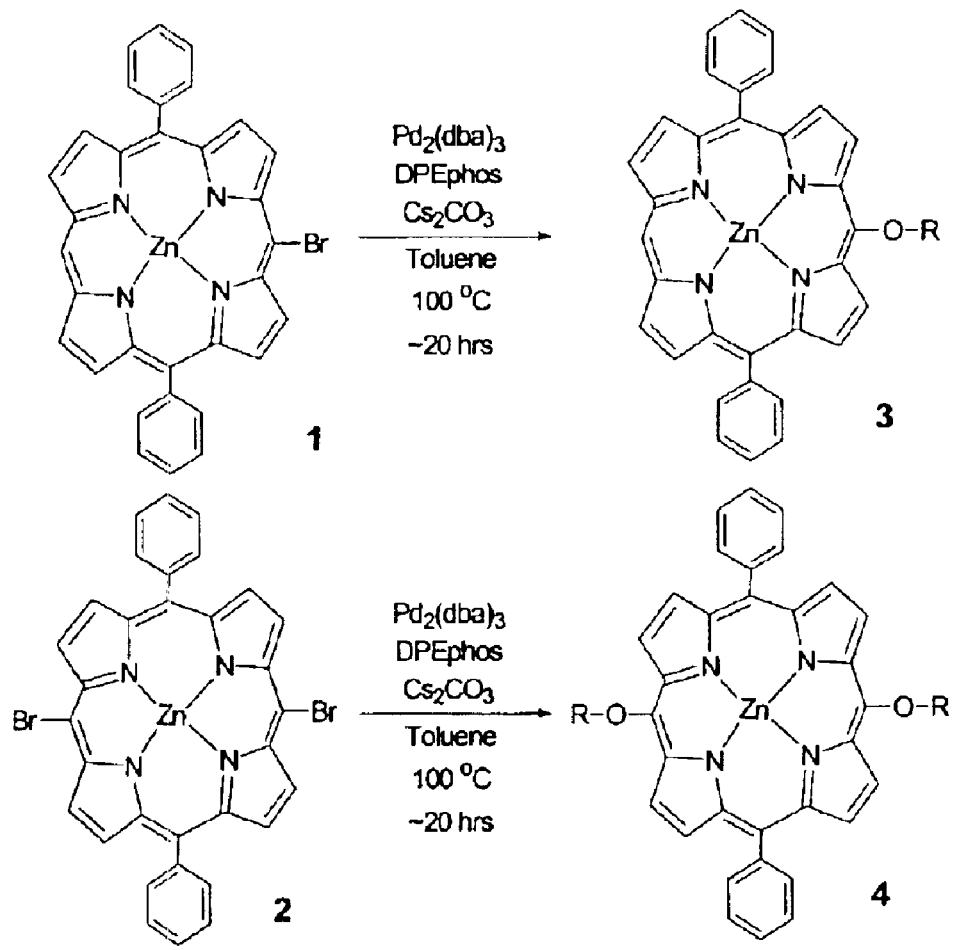
FIG. 6 illustrates a general reaction scheme whereby [5-bromo-10,20-diphenylporphyrino]zinc(II) (indicated in the Figure as compound 1) and [5,15-dibromo-10,20-diphenylporphyrino]zinc(II) (indicated in the Figure as Compound 2) undergo a palladium-catalyzed cross-coupling reaction to yield the corresponding meso-substituted phenoxyporphyrins (indicated in the Figure as compounds 3 and 4, respectively).
Figure 7:
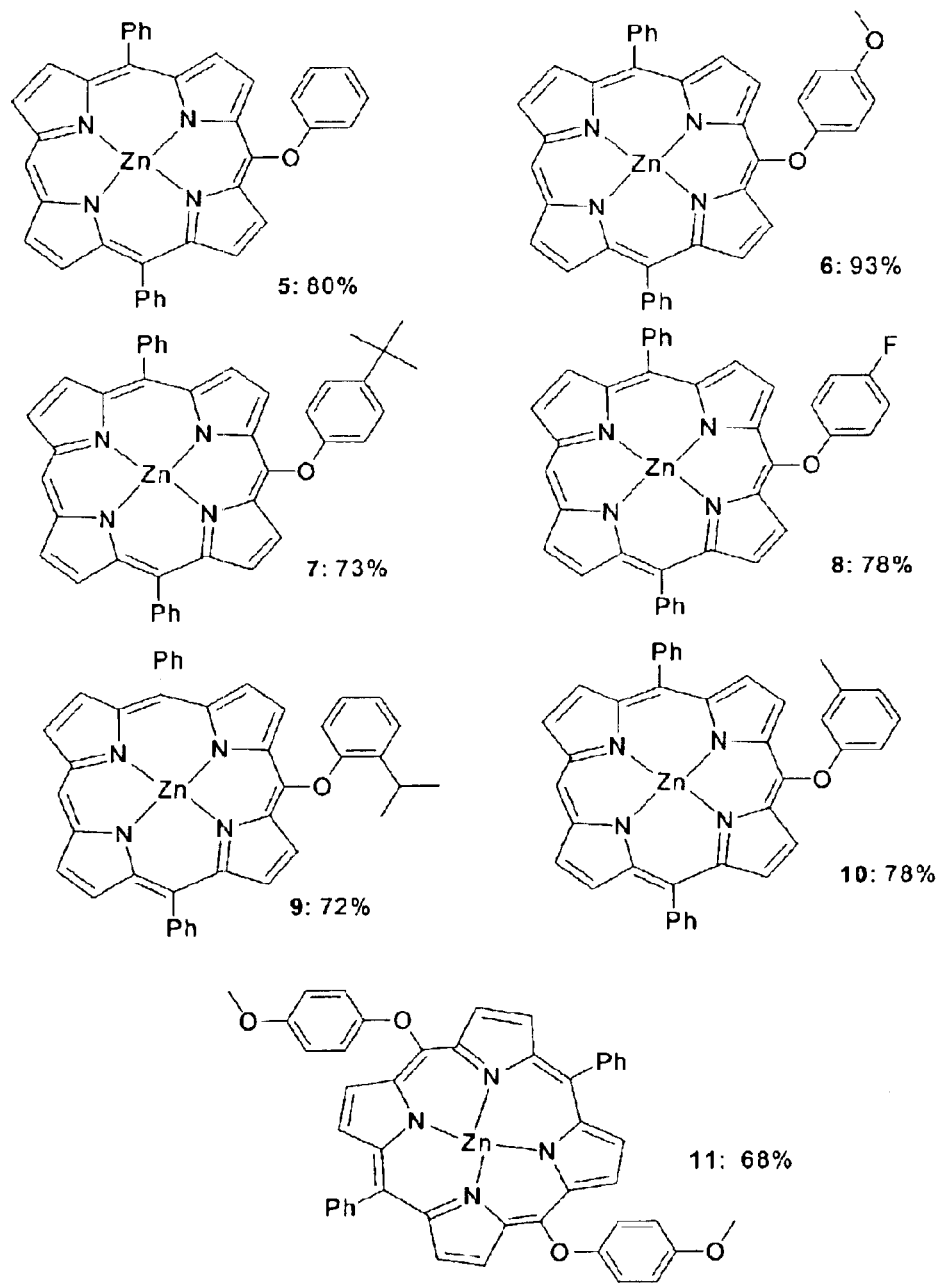
FIG. 7 shows the chemical structures of several heteroatom-substituted phenoxyporphyrin compounds of the present invention, which compounds are synthesized via the methods described herein.

In still a third embodiment of the invention, monobromoporphyrin [5-bromo-10,20-diphenylporphyrino]zinc(II) and the dibromoporphyrin [5,15-dibromo-10,20-diphenylporphyrino]zinc(II) may undergo efficient cross-coupling reactions with various phenols under mild conditions to yield desired phenoxy- and diphenoxy-substituted porphyrins. FIG. 6 illustrates the etheration of monobromoporphyrin [5-bromo-10,20-diphenylporphyrino]zinc(II) and the dibromoporphyrin [5,15-dibromo-10,20-diphenylporphyrino]zinc(II) using a combination of Pd(OAc)₂ or Pd₂(dba)₃ and a phosphine ligand as the catalyst. FIG. 7 illustrates the chemical structures a variety of phenoxy- and diphenoxy-substituted porphyrins that are obtained in the practice of the present invention.

LABORATORY EXAMPLES

The following Laboratory Examples have been included to illustrate preferred modes of the invention. Certain aspects of the following Laboratory Examples are described in terms of techniques and procedures found or contemplated by the present co-inventors to work well in the practice of the invention. These Laboratory Examples are exemplified through the use of standard laboratory practices of the co-inventors. In light of the present disclosure and the general level of skill in the art, those of skill will appreciate that the following Laboratory Examples are intended to be exemplary only, and that numerous changes, modifications and alterations can be employed without departing from the spirit and scope of the invention.

Examples 1–21 relate to methods of the present invention whereby substituted porphyrins with directly appended arylamino or alkylamino groups are synthesized using palladium catalyzed amination.

Example 1
General Considerations

All reactions were carried out under a nitrogen atmosphere in oven-dried glassware using standard Schlenk techniques. Tetrahydrofuran was distilled under nitrogen from sodium benzophenone ketyl. 5-Bromo-10,20-diphenylporphyrine and 5,15-dibromo-10,20-diphenylporphyrine as well as their corresponding zinc complexes [5-bromo-10,20-diphenylporphyrino]zinc(II) and [5,15-dibromo-10,20-diphenylporphyrino]zinc(II) were synthesized by literature methods. Bis(2-diphenylphosphinophenyl)ether (DPEphos), palladium(II) acetate and tris(dibenzylideneacetone) dipalladium(0) were purchased from Strem Chemical Co. Cesium carbonate was obtained as a gift from Chemetall Chemical Products, Inc. Proton and carbon nuclear magnetic resonance spectra ($^1$H NMR and $^{13}$C NMR) were recorded on a Varian Mercury 300 spectrometer and referenced with respect to residual solvent. Infrared spectra were obtained using a Bomen B100 Series FT-IR spectrometer. Samples were prepared as films on a NaCl plate by evaporating THF solutions. UV-Vis spectra were obtained using a Hewlett-Packard 8452A diode array spectrophotometer. High-resolution mass spectroscopy was performed by the Mass Spectrometry Center located in the Chemistry Department of the University of Tennessee on a VG Analytical hybrid high performance ZAB-EQ (B-E-Q geometry) instrument using electron impact (EI) ionization technique with a 70 eV electron beam. Thin layer chromatography was carried out on E. Merck Silica Gel 60 F-254 TLC plates.

Example 2

General Procedures for Amination of Bromoporphyrin

The bromoporphyrin, palladium precursor, phosphine ligand and base were placed in an oven-dried, resealable Schlenk tube. The tube was capped with a Teflon screwcap, evacuated, and backfilled with nitrogen. The screwcap was replaced with a rubber septum, and amine was added via syringe, followed by solvent. The tube was purged with nitrogen for 2 min, and then the septum was replaced with the Teflon screwcap. The tube was sealed, and its contents were heated with stirring until the starting bromoporphyrin had been completely consumed as indicated by TLC analysis. The resulting mixture was cooled to room temperature, taken up in ethyl acetate (60 mL) and transferred to a separatory funnel. The mixture was washed with water (×2), dried over anhydrous sodium sulfate, filtered and concentrated in vacuo. The crude product was then purified.

Example 3

Synthesis of [5-(N-Phenylamino)-10,20-diphenylporphvrino]zinc(II) (Table 1, Product 3a)

The general procedure was used to couple [5-bromo-10,20-diphenylporphyrino]zinc(II) (30 mg, 0.050 mmol) with aniline (17 μL, 0.18 mmol), using palladium acetate (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 13 h. The title compound was isolated by flash column chromatography (silica gel, ethyl acetate:hexanes (v)=1:4) as purple solids (29 mg, 95%). $^1$H NMR (300 MHz, THF-d$_8$): δ 10.08 (s, 1H), 9.48 (d, J=4.8 Hz, 2H), 9.31 (s, 1H), 9.29 (d, J=4.8 Hz, 2H), 8.92 (d, J=4.8 Hz, 2H), 8.81 (d, J=4.8 Hz, 2H), 8.22 (m, 4H), 7.75 (m, 6H), 7.04 (t, J=7.2 Hz, 2H), 6.87 (d, J=7.5 Hz, 2H), 6.65 (t, J=7.2 Hz, 1H). $^{13}$C NMR (75 MHz, THF-d$_8$): δ 164.8, 161.0, 160.8, 160.4, 160.2, 154.0, 145.1, 142.4, 141.7, 139.4, 139.2, 137.6, 136.8, 130.3, 130.2, 127.9, 124.6, 115.4. IR (film, cm$^{-1}$): 3383, 3050, 2953, 1599, 1493, 1307, 1061, 996, 793, 748. UV-vis (THF, λ$_{max}$, nm): 422, 554, 602. HRMS-EI ([M]$^+$): calcd for C$_{38}$H$_{25}$N$_5$Zn, 615.1401; found: 615.1382 with an isotope distribution pattern that is same as the calculated one.

Example 4

Synthesis of 5-(N-Phenylamino)-10,20-diphenylporphyrin (Table 1, Product 3b)

The general procedure was used to couple 5-bromo-10,20-diphenylporphyrin (27 mg, 0.05 mmol) with aniline (17 μL, 0,18 mmol), using palladium acetate (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 19 h. The title compound was isolated by flash chromatography (silica gel, ethyl acetate-:hexanes (v)=1:4) as red solids (27 mg, 98%). $^1$H NMR (300 MHz, THF-d$_8$): δ 10.14 (s, 1H), 9.44 (d, J=4.8 Hz, 2H), 9.42 (s, 1H), 9.30 (d, J=4.8 Hz, 2H), 8.90 (d, J=4.8 Hz, 2H), 8.77 (d, J=4.8 Hz, 2H), 8.21 (m, 4H), 7.78 (m, 6H), 7.06 (t, J=7.4, 2H), 6.86 (d, J=7.4 Hz, 2H), 6.69 (J=7.4 Hz, 1H), −2.54 (s, 2H). $^{13}$C NMR (75 MHz, THF-d$_8$): δ 154.8, 147.7, 142.7, 135.5, 132.1, 131.9, 131.1, 129.7, 128.5, 127.7, 120.6, 120.1, 119.0, 115.5, 105.1. IR (film, cm$^{-1}$): 3302, 3043, 1599, 1495, 1476, 1338, 1309, 1255, 1064, 973, 958, 797, 748. UV-vis(THF, λ$_{max}$, nm): 412, 512, 582, 660. HRMS-EI ([M]$^+$): calcd for C$_{38}$H$_{27}$N$_5$, 553.2266; found: 553.2274 with an isotope distribution pattern that is same as the calculated one.

Example 5

Synthesis of [5-(N-Methyl-N-phenylamino)-10,20-diphenylporphyrino]zinc(II) (Table 1, Product 4a)

The general procedure was used to couple [5-bromo-10,20-diphenylporphyrino]zinc(II) (30 mg, 0.050 mmol) with N-methylaniline (20 μL, 0.18 mmol), using palladium acetate (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 13 h. The title compound was isolated by flash column chromatography (silica gel, THF:hexanes (v)=1:8) as purple solids (31 mg, 99%). $^1$H NMR (300 MHz, THF-d$_8$): δ 10.20 (s, 1H), 9.36 (d, J=4.8 Hz, 2H), 9.19 (d, J=4.8 Hz, 2H), 8.97 (d, J=4.8 Hz, 2H), 8.87 (d, J=4.8 Hz, 2H), 8.23 (m, 4H), 7.77 (m, 6H), 7.05 (broad, 2H), 6.69 (broad, 2H), 6.61 (t, J=7.2 Hz, 1H), 4.28 (s, 3H). $^{13}$C NMR (75 MHz, THF-d$_8$): δ 156.0, 152.0, 151.2, 150.9, 150.7, 144.2, 135.5, 133.0, 132.8, 132.4, 130.0, 129.3, 128.1, 127.2, 125.3, 120.8, 116.7, 114.1, 106.9, 45.7. IR (film, cm$^{-1}$): 3054, 3023, 2978, 2876, 2807, 1596, 1498, 1341, 1120, 994, 793, 747. UV-vis (THF, λ$_{max}$, nm): 416, 552, 598. HRMS-EI ([M]$^+$): calcd for C$_{39}$H$_{27}$N$_5$Zn, 629.1558; found: 629.1549 with an isotope distribution pattern that is same as the calculated one.

Example 6

Synthesis of 5-(N-Methyl-N-phenylamino)-10,20-diphenylporphyrin (Table 1, Product 4b)

The general procedure was used to couple 5-bromo-10,20-diphenylporphyrin (54 mg, 0.10 mmol) with N-methylaniline (40 μL, 0.36 mmol), using palladium acetate (1.1 mg, 0.005 mmol) as the palladium precursor, DPEphos (4.0 mg, 0.0075 mmol) as the phosphine ligand and cesium carbonate (45.6 mg, 0.014 mmol) as the base. The reaction was conducted in THF (5 mL) at 68° C. for 16 h. The title compound was isolated by flash column chromatography (silica gel, ethyl acetate:hexanes (v)=1:4) as purple solids (53 mg, 94%). $^1$H NMR (300 MHz, CDCl$_3$): δ 10.18 (s, 1H), 9.30 (d, J=4.8 Hz, 2H), 9.19 (d, J=4.8 Hz, 2H), 9.00 (d, J=4.8 Hz, 2H), 8.90 (d, J=4.8 Hz, 2H), 8.23 (m, 4H), 7.78 (m, 6H), 7.19 (broad, 2H), 6.73 (broad, 3H), 4.26 (s, 3H), −2.82 (s, 2H). $^{13}$C NMR (75 MHz, CDCl$_3$): δ 154.9, 141.6, 134.9, 131.9, 131.7, 131.6, 129.6, 129.1, 128.0, 127.2, 124.2, 119.8, 116.9, 113.9, 105.8, 45.5. IR (film, cm$^{-1}$): 3303, 3055, 3026, 2875, 2810, 1596, 1498, 1351, 1113, 971, 796, 731. UV-vis (CHCl$_3$, λ$_{max}$, m): 410, 512, 548, 592. HRMS-EI ([M]$^+$): C$_{39}$H$_{29}$N$_5$, 567.2423; found: 567.2419 with an isotope distribution pattern that is same as the calculated one.

Example 7

Synthesis of [5-Benzophenoeimino-10,20-diphenylporphyrino]zinc(II) (Table 1, Product 5a)

The general procedure was used to couple [5-bromo-10,20-diphenylporphyrino]zinc(II) (30 mg, 0.050 mmol) with benzophenone imine (31 μL, 0.18 mmol), using palladium acetate (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 22 h. The title compound was isolated by flash column chromatography (silica gel, ethyl acetate:hexanes (v)=1:4) as purple solids (33 mg, 94%). $^1$H NMR (300 MHz, THF-d$_8$): δ 9.80 (s, 1H), 9.23 (d, J=4.8 Hz, 2H), 9.13 (d, J=4.8 Hz, 2H), 8.79 (d, J=4.8 Hz, 2H), 8.71 (d, J=4.8 Hz, 2H), 8.19 (broad, 6H), 7.73 (m, 6H), 7.66 (broad, 3H), 7.36 (broad, 2H), 6.65 (broad, 3H). $^{13}$C NMR (75 MHz, THF-d$_8$): δ 170.8, 152.0, 150.3, 149.9, 144.5, 142.5, 135, 4, 133.0, 131.6, 131.1, 130.9, 130.0, 129.4, 128.8, 127.9, 127.2, 120.6, 103.7. IR (film, cm$^{-1}$): 3056, 3023, 2962, 1618, 1596, 1578, 1490, 1439, 1124, 1061, 994, 794. UV-vis (THF, λ$_{max}$, nm): 428, 562, 610. HRMS-EI ([M]$^+$): calcd for C$_{45}$H$_{29}$N$_5$Zn, 703.1714; found: 703.1699 with an isotope distribution pattern that is same as the calculated one.

Example 8

Synthesis of 5-Benzophenoeimino-10,20-diphenylporphyrin (Table 1, Product 5b)

The general procedure was used to couple 5-bromo-10,20-diphenylporphyrin (27 mg, 0.05 mmol) with benzophenone imine (31 μL, 0.18 mmol), using palladium acetace (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 24 h. The title compound was isolated by flash column chromatography (silica gel, ethyl acetate: hexanes (v)=1:8) as purple solids (27 mg, 84%). $^1$H NMR (300 MHz, CDCl$_3$): δ 9.78 (s, 1H), 9.23 (d, J=4.8 Hz, 2H), 9.08 (d, J=4.8 Hz, 2H), 8.85 (d, J=4.8 Hz, 2H), 8.75 (d, J=4.8 Hz, 2H), 8.26 (broad, 6H), 7.76 (broad, 9H), 7.18 (broad, 2H), 6.61 (broad, 3H), −2.34 (s, 2H). $^{13}$C NMR (75 MHz, CDCl$_3$): δ 171.6, 146.0, 141.7, 134.6, 133.6, 131.6, 130.7, 129.8, 127.9, 127.5, 126.8, 119.4, 102.4. IR (film, cm$^{-1}$): 3306, 3057, 3026, 1808, 1616, 1595, 1576, 1476, 1442, 1405, 1316, 1241, 1097, 976, 954, 845, 797, 745. UV-vis (CHCl$_3$, λ$_{max}$, nm): 424, 526, 564, 604, 658. HRMS-EI ([M]$^+$): calcd for C$_{45}$H$_{31}$N$_5$, 641.2579; found: 641.2591 with an isotope distribution pattern that is same as the calculated one.

Example 9

Synthesis of [5-(N-Diphenylamino)-10,20-diphenylporphyrino]zinc(II) (Table 1, Product 6a)

The general procedure was used to couple [5-bromo-10,20-diphenylporphyrino]zinc(II) (30 mg, 0.05 mmol) with diphenylamine (0.031 g, 0.18 mmol), using palladium acetate (1.1 mg, 0.005 mmol) as the palladium precursor, DPEphos (4.0 mg, 0.0075 mmol) as the phosphine ligand and sodium tert-butoxide (13.5 mg, 0.14 mmol) as the base. The reaction was conducted in THF (5 mL) at 68° C. for 25 h. The title compound was isolated by flash column chromatography (silica gel, THF: hexanes (v)=1:6) as purple solids (21 mg, 61%). $^1$H NMR (300 MHz, THF-d$_8$): δ 10.17 (s, 1H), 9.33 (m, 4H), 8.93 (d, J=4.8 Hz, 2H), 8.80 (d, J=4.8 Hz, 2H), 8.20 (m, 4H), 7.75 (m, 6H), 7.33 (m, 8H), 7.12 (t, J=7.8 Hz, 8H), 6.80 (t, J=7.2 Hz, 4H). $^{13}$C NMR (75 MHz, CDCl$_3$): δ 153.7, 153.0, 151.3, 151.0, 150.1, 144.1, 135.4, 133.3, 132.8, 132.4, 130.9, 129.8, 129.6, 128.1, 127.2, 122.9, 121.1, 120.9, 107.0. IR (film, cm$^{-1}$): 3055, 2961, 2361, 1598, 1587, 1490, 1293, 1273, 1062, 1003, 994, 794, 752. UV-vis (THF, λ$_{max}$, nm): 412, 558, 604. HRMS-EI ([M]$^+$): calcd for C$_{44}$H$_{29}$N$_5$Zn, 691.1714; found: 691.1712 with an isotope distribution pattern that is same as the calculated one.

Example 10

Synthesis of 5-(N-Diphenylamino)-10,20-diphenylporphyrin (Table 1, Product 6b)

The general procedure was used to couple 5-bromo-10,20-diphenylporphyrin (54 mg, 0.1 mmol) with diphenylamine (0.061 g, 0.36 mmol), using palladium acetate (1.1 mg, 0.005 mmol) as the palladium precursor, DPEphos (4.0 mg, 0.0075 mmol) as the phosphine ligand and cesium carbonate (45.6 mg, 0.014 mmol) as the base. The reaction was conducted in THF (5 mL) at 68° C. for 40 h. The title compound was isolated by flash column chromatography (silica gel, THF: hexanes (v)=1:8) as purple solids (41 mg, 66%). $^1$H NMR (300 MHz, CDCl$_3$): δ 10.13 (s, 1H), 9.33 (d, J=4.8 Hz, 2H), 9.26 (d, J=4.8 Hz, 2H), 8.96 (d, J=4.8 Hz, 2H), 8.83 (d, J=4.8 Hz, 2H), 8.20 (m, 4H), 7.76 (m, 6H), 7.35 (m, 4H), 7.20 (t, J=7.2 Hz, 4H), 6.89 (t, J=7.2 Hz, 2H), −2.69 (s, 2H). $^{13}$C NMR (75 MHz, CDCl$_3$): δ 152.5, 141.3, 134.8, 134.6, 132.0, 131.4, 130.1, 129.1, 127.8, 126.8, 122.3, 120.8, 119.6, 105.6. IR (film, cm$^{-1}$): 3307, 3055, 3029, 1591, 1491, 1342, 1184, 973, 796, 750, 731, 695. UV-vis (CHCl$_3$, λ$_{max}$, nm): 407, 523, 577, 656. HRMS-EI ([M]$^+$): calcd for C$_{44}$H$_{31}$N$_5$, 629.2579; found: 629.2576 with an isotope distribution pattern that is same as the calculated one.

Example 11

Synthesis of [5-(N-Hexylamino)-10,20-diphenylporphyrino]zinc(II) (Table 1, Product 7a)

The general procedure was used to couple [5-bromo-10,20-diphenylporphyrino]zinc(II) (30 mg, 0.05 mmol) with hexylamine (0.024 ml, 0.18 mmol), using palladium acetate (0.55 mg, 0.0025 mmol) as the palladium precursor, DPEphos (2.0 mg, 0.0038 mmol) as the phosphine ligand and cesium carbonate (22.8 mg, 0.070 mmol) as the base. The reaction was conducted in THF (5 mL) at 68° C. for 50 h.

The title compound was isolated by flash column chromatography (silica gel, THF: hexanes (v)=1:8) as purple solids (25 mg, 80%). $^1$H NMR (300 MHz, THF-d$_8$): δ 9.63 (s, 1H), 9.43 (d, J=4.8 Hz, 2H), 9.05 (d, J=4.8 Hz, 2H), 8.76 (d, J=4.8 Hz, 2H), 8,65 (d, J=4.8 Hz, 2H), 8.18 (m, 4H), 7.75 (m, 6H), 7.33 (m, 8H), 6.78 (s, 1H), 4.38 (m, 2H), 2.04 (m, 2H), 1.58 (m, 2H), 1.37 (m, 4H), 0.87 (t, J=7.2 Hz, 3H). $^{13}$C NMR (75 MHz, THF-d$_8$): δ 152.7, 149.9, 149.5, 147.0, 144.7, 135.3, 133.0, 131.4, 130.2, 127.8, 127.2, 126.9, 120.5, 102.4, 60.2, 32.8, 32.5, 28.0, 23.5, 14.4. IR (film, cm$^{-1}$): 3330, 3053, 2954, 2925, 2854, 1584, 1542, 1489, 1440, 1213, 1062, 1010, 1002, 992, 836, 789, 780, 750. UV-vis (THF, λ$_{max}$, nm): 428, 606. HRMS-EI ([M]$^+$): calcd for C$_{38}$H$_{33}$N$_5$Zn, 623.2027; found: 623.2009 with an isotope distribution pattern that is same as the calculated one.

Example 12

Synthesis of [5,15-Bis(N-phenylamino)-10,20-diphenylporphyrino]zinc(II) (Table 1, Product 8a)

The general procedure was used to couple [5,15-dibromo-10,20-diphenylporphyrino]zinc(II) (34 mg, 0.050 mmol) with aniline (22 µL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 13 h. The title compound was isolated by flash column chromatography (silica gel, THF:hexanes (v)=1:4) as purple solids (29 mg, 82%). $^1$H NMR (300 MHz, THF-d$_8$): δ 9.36 (d, J=4.8 Hz, 4H), 9.17 (s, 2H), 8.69 (d, J=4.8 Hz, 4H), 8.16 (m, 4H), 7.72 (m, 6H), 7.03 (t, J=6.9, 7.2 Hz, 4H), 6.84 (d, J=8.4 Hz, 4H), 6.64 (t, J=7.2 Hz, 2H). $^{13}$C NMR (75 MHz, THF-d$_8$): δ 155.1, 152.0, 150.5, 144.4, 135.3, 132.2, 129.7, 129.6, 128.0, 127.2, 121.0, 119.9, 118.2, 115.0. IR (film, cm$^{-1}$): 3380, 3047, 3020, 2953, 1599, 1492, 1339, 1308, 1063, 1003, 795, 747. UV-vis (THF, λ$_{max}$, nm): 440, 564, 620. HRMS-EI ([M]$^+$): calcd for C$_{44}$H$_{30}$N$_6$Zn, 706.1823; found: 706.1840 with an isotope distribution pattern that is same as the calculated one.

Example 13

Synthesis of 5,15-Bis(N-phenylamino)-10,20-diphenylporphrin (Table 1, Product 8b)

The general procedure was used to couple 5,15-dibromo-10,20-diphenylporphyrin (31 mg, 0.05 mmol) with aniline (22 µL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 20 h. The title compound was isolated by flash column chromatography (silica gel, ethyl acetate:hexanes (v)=1:4) as purple solids (21 mg, 65%). $^1$H NMR (300 MHz, THF-d$_8$): δ 9.32 (d, J=4.8 Hz, 4H), 9.29 (s, 2H), 8.65 (d, J=4.8 Hz, 4H), 8.17 (m, 4H), 7.75 (m, 6H), 7.07 (t, J=8.1 Hz, 4H), 6.86 (d, J=8.1 Hz, 4H), 6.69 (t, J=7.4 Hz, 2H), −2.03 (s, 2H). $^{13}$C NMR (75 MHz, THF-d$_8$): δ 154.5, 142.9, 137.1, 135.3, 129.7, 128.5, 127.6, 120.5, 119.7, 118.9, 115.4. IR (film, cm$^{-1}$): 3307, 1599, 1496, 1474, 1340, 1306, 1258, 1071, 974, 797, 732. UV-vis (THF, λ$_{max}$, nm): 438, 526, 592, 680. HRMS-EI ([M]$^+$): calcd for C$_{44}$H$_{32}$N$_6$, 644.2688; found: 644.2704 with an isotope distribution pattern that is same as the calculated one.

Example 14

Synthesis of [5,15-Bis(N-methyl-N-phenylamino)-10,20-diphenylporphyrino]zinc(II) (Table 1, Product 9a)

The general procedure was used to couple [5,15-dibromo-10,20-diphenylporphyrino]zinc(II) (34 mg, 0.050 mmol) with N-methylaniline (26 µL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 17 h. The title compound was isolated by flash column chromatography (silica gel, THF:hexanes (v)=1:8) as purple solids (30 mg, 82%). $^1$H NMR (300 MHz, THF-d$_8$): δ 9.10 (d, J=4.8 Hz, 4H), 8.75 (d, J=4.8 Hz, 4H), 8.15 (m, 4H), 7.73 (m, 6H), 7.04 (broad, 4H), 6.69 (broad, 4H), 6.59 (t, J=7.2 Hz, 2H), 4.25 (s, 6H). $^{13}$C NMR (75 MHz, THF-d$_8$): δ 155.8, 152.4, 150.9, 144.0, 135.2, 133.1, 130.1, 129.3, 128.2, 127.2, 125.7, 121.2, 116.8, 114.2, 45.6. IR (film, cm$^{-1}$): 3054, 2985, 2883, 2807, 1597, 1496, 1346, 1118, 1000, 796, 747. UV-vis (THF, λ$_{max}$, nm): 422, 562, 608. HRMS-EI ([M]$^+$): calcd for C$_{46}$H$_{34}$N$_6$Zn, 734.2136; found: 734.2128 with an isotope distribution pattern that is same as the calculated one.

Example 15

Synthesis of 5,15-Bis(N-methyl-N-phenylamino)-10,20-diphenylporphyrin (Table 1, Product 9b)

The general procedure was used to couple 5,15-dibromo-10,20-diphenylporphyrin (31 mg, 0.05 mmol) with N-methylaniline (26 µL, 0.24 mmol), using palladium acetate (1.1 mg, 0.0050 mmol) as the palladium precursor, DPEphos (4.0 mg, 0.0075 mmol) as the phosphine ligand and the cesium carbonate (45.6 mg, 0.14 mmol) as the base. The reaction was conducted in THF (5 mL) at 68° C. for 15 h. The title compound was isolated by flash column chromatography (silica gel, ethyl acetate: hexanes (v)=1:4) as red solids (24 mg, 71%). $^1$H NMR (300 MHz, CDCl$_3$): δ 9.08 (d, J=4.8 Hz, 4H), 8.77 (d, J=4.8 Hz, 4H), 8.16 (m, 4H), 7.72 (m, 6H), 7.14 (m, 4H), 6.72 (m, 6H), 4.23 (s, 6H), −2.54 (s, 2H). $^{13}$C NMR (75 MHz, CDCl$_3$): δ 154.4, 141.3, 134.5, 131.9, 128.9, 128, 127.8, 126.8, 124.3, 119.9, 116.7, 113.8, 45.1. IR (film, cm$^{-1}$): 3315, 3026, 2359, 1596, 1498, 1475, 1354, 1114, 972, 798. UV-vis (CHCl$_3$, λ$_{max}$, nm): 412, 522, 562, 596, 608. HRMS-EI ([M]$^+$): calcd for C$_{46}$H$_{36}$N$_6$, 672.3001; found: 672.3003 with an isotope distribution pattern that is same as the calculated one.

Example 16

Synthesis of [5,15-Bis(benzophenoeimino)-10,20-diphenylporphyrino]zinc(II) (Table 1, Product 10a)

The general procedure was used to couple [5,15-dibromo-10,20-diphenylporphyrino]zinc(II) (34 mg, 0.050 mmol) with benzophenoe imine (41 µL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 16 h. The title compound was isolated by flash column chromatography (silica gel, ethyl acetate:hexanes (v)=1:4) as purple solids (37 mg, 84%). $^1$H NMR (300 MHz, CDCl$_3$): δ 9.06 (d, J=4.8 Hz, 4H), 8.57 (d, J=4.8 Hz, 4H), 8.19 (m, 4H), 8.07 (m, 4H), 7.68 (m, 6H), 7.61 (m, 6H), 7.33 (m, 4H), 6.62 (m, 6H). $^{13}$C NMR (75 MHz, CDCl$_3$): δ 170.8, 149.4, 144.7, 143.8, 135.4, 135.2, 132.7, 131.9, 131.5, 130.8, 129.9, 129.3, 128.4, 128.0, 127.7, 127.2, 127.1, 126.9, 120.9. IR (film, cm$^{-1}$): 3054, 3027, 2976, 1618, 1597, 1485, 1442, 1338, 1212, 1118, 1004, 793, 753. UV-vis (THF, λ$_{max}$, nm): 438, 652. HRMS-EI ([M]$^+$): calcd for C$_{58}$H$_{38}$N$_6$Zn, 882.2449, found: 882.2464 with an isotope distribution pattern that is same as the calculated one.

Example 17

Synthesis of 5,15-Bis(benzophenoeimino-10,20-diphenylporphyrin (Table 1, Product 10b)

The general procedure was used to couple 5,15-dibromo-10,20-diphenylporphyrin (31 mg, 0.05 mmol) with benzophenoe imine (41 μL, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 15 h. The title compound was isolated by flash column chromatography (silica gel, ethyl acetate: hexanes (v)=1:4) as purple solids (39 mg, 95%). $^1$H NMR (300 MHz, THF-d$_8$): δ 9.09 (d, J=4.8 Hz, 4H), 8.57 (d, J=4.8 Hz, 4H), 8.10 (m, 8H), 7.64 (m, 12H), 7.23 (broad, 4H), 6.62 (broad, 6H), −1.87 (s, 2H). $^{13}$C NMR (75 MHz, THF-d$_8$): δ 172.3, 143.2, 140.8, 137.9, 135.4, 135.1, 132.1, 131.0, 129.3, 128.9, 128.3, 128.2, 127.5, 120.3, 108.4. IR (film, cm$^{-1}$) 3316, 3056, 3022, 1614, 1596, 1575, 1465, 1443, 1351, 1316, 1278, 1244, 1105, 1066, 976, 950, 798, 725. UV-vis (THF, λ$_{max}$, nm): 434, 592, 700. HRMS-EI ([M]$^+$): calcd for C$_{58}$H$_{40}$N$_6$, 820.3314; found: 820.3308 with an isotope distribution pattern that is same as the calculated one.

Example 18

Synthesis of [5,15-Bis(N-diphenylamino)-10,20-diphenylporphyrino]zinc(II) (Table 1, Product 11a)

The general procedure was used to couple [5,15-dibromo-10,20-diphenylporphyrino]zinc(II) (34 mg, 0.05 mmol) with diphenylamine (0.041 g, 0.24 mmol), using palladium acetate (1.1 mg, 0.0050 mmol) as the palladium precursor, DPEphos (4.0 mg, 0.0075 mmol) as the phosphine ligand and sodium tert-butoxide (13.5 mg, 0.14 mmol) as the base. The reaction was conducted in THF (5 mL) at 68° C. for 50 h. The title compound was isolated by flash column chromatography (silica gel, THF: hexanes (v)=1:6) as purple solids (13 mg, 30%). $^1$H NMR (300 MHz, CDCl$_3$): δ 9.25 (d, J=4.8 Hz, 4H), 8.75 (d, J=4.8 Hz, 4H), 8.09 (m, 4H), 7.66 (m, 6H), 7.29 (m, 8H), 7.15 (t, J=7.8 Hz, 8H), 6.85 (t, J=7.4 Hz, 4H). $^{13}$C NMR (75 MHz, CDCl$_3$): δ 152.6, 152.3, 149.7, 142.1, 134.3, 133.3, 130.5, 129.1, 127.6, 126.5, 122.8, 122.1, 121.0, 120.7. IR (film, cm$^{-1}$): 3056, 2360, 1595, 1590, 1490, 1341, 1294, 1249, 1002, 794, 750. UV-vis (CHCl$_3$, λ$_{max}$, nm): 406, 460, 572, 628. HRMS-EI ([M]$^+$): calcd for C$_{56}$H$_{38}$N$_6$Zn, 858.2449; found: 858.2436 with an isotope distribution pattern that is same as the calculated one.

Example 19

Synthesis of [5,15-Bis(N-4-trifluoromethylphenylamino)-10,20-diphenylporphyrino]zinc(II) (Table 1, Product 12a)

The general procedure was used to couple [5,15-dibromo-10,20-diphenylporphyrino]zinc(II) (34 mg, 0.05 mmol) with 4-trifluoromethyllaniline (0.030 ml, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 17 h. The title compound was isolated by flash column chromatography (silica gel, ethyl acetate: hexanes (v)=1:2) as purple solids (38 mg, 90%). $^1$H NMR (300 MHz, THF-d$_8$): δ 9.84 (s, 2H), 9.43 (d, J=4.8 Hz, 4H), 8.84 (d, J=4.8 Hz, 4H), 8.22 (m, 4H), 7.78 (m, 6H), 7.41 (d, J=8.2 Hz, 4H), 6.93 (d, J=8.2 Hz, 4H). $^{13}$C NMR (75 MHz, THF-d$_8$): δ 157.5, 151.7, 151.0, 144.1, 135.4, 132.9, 129.7, 128.2, 127.3, 127.2, 127.1, 121.6, 119.3, 118.1, 114.1. IR (film, cm$^{-1}$): 3376, 1614, 1522, 1322, 1110, 1065, 1003, 828, 797. UV-vis (THF, λ$_{max}$, nm): 435, 562, 612. HRMS-EI ([M]$^+$): calcd for C$_{46}$H$_{28}$N$_6$F$_6$Zn, 842.1571; found: 842.1590 with an isotope distribution pattern that is same as the calculated one.

Example 20

[5,15-Bis(N-4-methoxyphenylamino)-10,20-diphenylporphyrino]zinc(II) (Table 1, Product 13a)

The general procedure was used to couple [5,15-dibromo-10,20-diphenylporphyrino]zinc(II) (34 mg, 0.05 mmol) with p-anisidine (30 mg, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 16 h. The title compound was isolated by flash column chromatography (silica gel, ethyl acetate: hexanes (v)=1:3 as purple solids (36 g, 94%). $^1$H NMR (300 MHz, THF-d$_8$): δ 9.34 (d, J=4.8 Hz, 4H), 8.88 (s, 2H), 8.66 (d, J=4.8 Hz, 4H), 8.17 (m, 4H), 7.73 (m, 6H), 6.87 (d, J=9.0 Hz, 4H), 6.69 (d, J=9.0 Hz, 4H), 3.65 (s, 6H). $^{13}$C NMR (75 MHz, THF-d$_8$): δ 153.5, 151.9, 150.2, 149.6, 144.6, 135.3, 131.9, 129.3, 127.8, 127.1, 121.2, 120.7, 116.6, 115.0, 55.6. IR (film, cm$^{-1}$): 3372, 1597, 1507, 1489, 1339, 1234, 1036, 1002, 797. UV-vis (THF, λ$_{max}$, nm): 447, 571, 629.

Example 21

Synthesis of [5,15-Bis(N-3,5-di-tert-butylphenylamino)-10,20-diphenylporphyrino]zinc (II) (Table 1, Product 14a)

The general procedure was used to couple [5,15-dibromo-10,20-diphenylporphyrino]zinc(II) (34 mg, 0.05 mmol) with 3,5-di-tert-butylaniline (0.050 g, 0.24 mmol), using palladium acetate (1.1 mg, 0.0050 mmol) as the palladium precursor, DPEphos (4.0 mg, 0.0075 mmol) as the phosphine ligand and cesium carbonate (45.6 mg, 0.14 mmol) as the base. The reaction was conducted in THF (5 mL) at 68° C. for 62 h. The title compound was isolated by flash column chromatography (silica gel, ethyl acetate: hexanes (v)=1:4) as purple solids (44 mg, 95%). $^1$H NMR (300 MHz, CDCl$_3$): δ 9.28 (d, J=4.8 Hz, 4H), 8.68 (d, J=4.8 Hz, 4H), 8.14 (m, 4H), 7.71 (m, 8H), 6.87 (m, 6H), 1.21 (s, 36H). $^{13}$C NMR (75 MHz, CDCl$_3$): δ 152.1, 151.5, 150.6, 149.4, 143.0, 134.8, 131.7, 128.5, 127.1, 126.4, 120.4, 118.8, 113.4, 109.6, 34.7, 31.3. IR (film, cm$^{-1}$): 3383, 3055, 2961, 2902, 2867, 1595, 1488, 1436, 1340, 1064, 1004, 796. UV-vis (THF, λ$_{max}$, nm): 448, 576, 634. HRMS-EI ([M]$^+$): calcd for C$_{60}$H$_{62}$N$_6$Zn, 930.4327; found: 930.4354 with an isotope distribution pattern that is same as the calculated one.

Examples 22 through 47 relate to methods of synthesizing aminophenylporphyrins, and novel aminophenylporphyrins, according to the present invention. In Example 22–47, ligand referred to by number refer to the numbered ligands shown in FIG. 2.

Example 22

General Considerations

All reactions were carried out under a nitrogen atmosphere in oven-dried Schlenk tube. All amines were purchased from Acros Organics or Aldrich Chemical Co. and used without further purification. Tetrahydrofuran and toluene were continuously refluxed and freshly distilled from sodium benzophenone ketyl under nitrogen. Sodium tert-butoxide was purchased from Aldrich Chemical Co.; Cesium carbonate was obtained as a gift from Chemetall Chemical Products, Inc.

Potassium phosphate, potassium carbonate, palladium(II) acetate, tris(dibenzylideneacetone)dipalladium(0), 2-(di-t-butylphosphino)biphenyl (FIG. 2, Ligand 1), 2-(dicyclohexylphosphino)biphenyl (FIG. 2, Ligand 2), 2-dicyclohexylphosphino-2'-(N,N-di-methylamino)biphenyl (FIG. 2, Ligand 4), bis(2-diphenylphosphinophenyl)ether (DPEphos, FIG. 2, Ligand 6), Xantphos (FIG. 2, Ligand 7), racemic-2-(di-t-butylphosphino)-1,1'-binaphthyl (FIG. 2, Ligand 8), (±)BINAP (FIG. 2, Ligand 9), dichloro[1,1'-bis(diphenylphosphino)ferrocene]palladium(II) dichloride ((dppf)PdCl$_2$, FIG. 2, Ligand 10) and 1,3-bis(2,6-di-1-propylphenyl)imidazolium chloride (FIG. 2, Ligand 11) were purchased from Strem Chemical Co.; 2-(dicyclohexylphosphino)-2'6'dimethyl-biphenyl (FIG. 2, Ligand 3) and the ligand shown in FIG. 2 as ligand 5 were synthesized according to literature methods. All ligands and palladium precursors and bases were stored in desiccators filled with anhydrous calcium sulfate, and weighed in the air. 5,15-di-p-bromophenylporphyrin as well as its zinc complex, and tetrakis-p-bromophenylporphyrin were prepared according to the method described in literatures. $^1$H NMR and $^{13}$C NMR were recorded on Varian Mercury 300 spectrometer with TMS as an internal standard. UV-Vis spectra were measured on Hewlett-Packard 8452 diode array spectrometer. High resolution mass spectroscopy was determined on a VG analytical hybrid high performance ZAB-EQ(B-E-Q geometry) instrument by the Mass Spectrometry Center (Department of Chemistry, University of Tennessee). All solvents were supplied by Fisher Scientific, Inc. with HPLC grade and used as received. Thin layer chromatography was performed on Silica Gel 60F-254 precasted aluminum TLC plate.

Example 23

General Procedures for Amination of Bromophenylporphyrin

An oven-dried Schlenk tube equipped with stirring bar was degassed on vacuum line and purged with nitrogen. The tube was charged with Pd(OAc)$_2$ or Pd$_2$(dba)$_3$ (5 mole %), phosphine ligand (10 mole %), bromophenylporphyrin or zinc complex (0.05 mmole), base (NaOtBu or Cs$_2$CO$_3$, 4.0 equiv for 1.0 equiv Br) and solid amine, if any. The tube was capped with a Teflon screw cap, evacuated on vacuum line for 40–50 min and backfilled with nitrogen. The Teflon screw cap was then replaced with a rubber septum, 2–3 mL of freshly redistilled and dried solvent, and amine (4.0 equiv for 1.0 equiv Br) was added via syringe successively. Additional 2–3 mL of solvent was added against the wall of the tube to wash down the possible reactants on the wall. The tube was purged with nitrogen for 1–2 min, and the septum was then replaced by Teflon screw cap. The tube was tightly sealed and immersed in a 100° C. oil bath. The reaction was preceded under this condition with stirring for 48 h (72 h for tetra-bromophenylporphyrin), and cooled to room temperature. The aliquot of the solution was detected on TLC (methylene chloride:hexanes=8:2 or ethyl acetate:hexanes=5:5) to monitor the result.

Example 24

General Workup Procedures for Amination of Bromophenylporphyrin

The reaction solution was transferred with a long glass pipet to a small round-bottom flask, the residue was washed with acetone or chloroform and pooled to the flask as well. The solution was concentrated on rotavapor to remove the solvent. The residue was redissolved in ethyl acetate and transferred to a separatory funnel, washed with deioned water three times to remove the base and salts. The organic layer was concentrated on rotavapor to dryness. The residue was dissolved in minimal acetone (or methylene chloride, or THF), and small amount of hexanes was added to recrystallize the product. The product gradually precipitated or crystallized from the solution, filtered on funnel, washed with small amount of hexanes to afford the pure product (purity 98–99%). Extra pure compound can be obtained through flash chromatography on silica gel column. (methylene chloride:hexanes (8:2 to 10:0) as elute).

Example 25

Synthesis of 5,15-di-p-(N-phenylamino) phenylporphyrin (Table 2, entry 1, A)

The general procedure using 5,15-di-p-bromophenylporphyrin (31.0 mg, 0.05 mmol), Pd(OAc)$_2$ (1.12 mg, 0.005 mmol), (±) BINAP (6.2 mg, 0.01 mmol, 9), Cs$_2$CO$_3$ (130.33 mg, 0.4 mmol), aniline (36.5 µl, 0.4 mmol) and toluene, the reaction proceeded at 100° C. for 48 h. After workup with general procedure, the title compound was obtained as dark-purple solid (22.6 mg, 70%). $^1$H NMR (CDCl$_3$, 300 MHz) δ 10.29 (s, meso-2H), 9.39 (d, J=4.5 Hz, β-4H), 9.17 (d, J=4.8 Hz, β-4H), 8.14 (d, J=8.7 Hz, 4H), 7.50 (d, J=8.4 Hz, 4H), 7.38–7.46 (m, 8H), 7.06 (m, 2H), 6.13 (s, 2H), −3.05 (s, 2). $^{13}$C NMR (CDCl$_3$, 75 MHz) 6142.9, 142.6, 135.9, 131.5, 131.0, 129.6, 121.6, 118.6, 115.7, 105.1. UV-vis ($\lambda_{max}$, nm) 421, 508, 548, 580, 637. HRMS-EI ([M+1]$^+$): calc'd for C$_{44}$H$_{33}$N$_6$, 645.2767; found 645.2734

Example 26

Synthesis of 5,15-di-p-(N-phenylamino) phenylporphyrin (Zn II) (Table 1, entry 1, B)

The reactants were as the same as entry 1 A except 5,15-di-p-bromophenylporphyrin was replaced by its zinc complex (34.5 mg, 0.05 mmol). After workup with general procedure, the title compound was obtained as brown solid (23.5 mg, 66%). $^1$H NMR (CDCl$_3$, 300 MHz) δ 10.31 (s, meso-2H), 9.45 (d, J=4.2 Hz, β-4H), 9.24 (d, J=4.5 Hz, β-4H), 8.14 (d, J=8.1 Hz, 4H), 7.50 (d, J=8.4 Hz, 4H), 7.40–7.47 (m, 8H), 7.06 (m, 2H), 6.11 (s, 2H). $^{13}$C NMR (CDCl$_3$, 75 MHz) δ 150.4, 149.3, 135.7, 132.5, 131.6, 129.5, 121.5, 118.4, 115.5, 106.1. UV-vis ($\lambda_{max}$, nm) 419, 542, 583. HRMS-EI ([M]$^+$): calc'd for C$_{44}$H$_{30}$N$_6$Zn, 706.1823; found 706.1845

Example 27

Synthesis of 5,15-di-p-[N-(4-nitrophenyl)amino] phenylporphyrin (Table 2, entry 2, A)

The general procedure using 5,15-di-p-bromophenylporphyrin (31.0 mg, 0.05 mmol), Pd(OAc)$_2$ (1.12 mg, 0.005 mmol), (±) BINAP (6.2 mg, 0.01 mmol, 9), Cs$_2$CO$_3$ (130.33 mg, 0.4 mmol), 4-nitroaniline (55.3 mg, 0.4 mmol) and toluene, the reaction proceeded at 100° C. for 48 h. After workup with general procedure, the title compound was obtained as brown solid (28.0 mg, 76%). $^1$H NMR (DMSO-d$_6$, 300 MHz) δ 10.64 (s, meso-2H), 9.82 (s, 2H), 9.67 (d, J=4.2 Hz, β-4H), 9.15 (d, J=4.2 Hz, β-4H), 8.24–8.29 (m, 8H), 7.75 (d, J=7.5 Hz, 4H), 7.45 (d, J=9.0

Hz, 4H), −3.19 (s, 2H). $^{13}$C NMR (DMSO-d$_6$, 75 MHz) δ 150.5, 146.7, 144.7, 140.2, 138.4, 135.9, 134.9, 132.7, 130.9, 126.4, 118.9, 114.3, 105.8. UV-vis (λ$_{max}$, nm) 413, 506, 542, 579, 635. HRMS-EI ([M+1]$^+$): calc'd for C$_{44}$H$_{31}$N$_8$O$_4$, 735.2463; found 725.2436.

Example 28

Synthesis of 5,15-di-p-[N-(4-methoxyphenyl)amino] phenylporphyrin (Table 2, entry 3, A)

The general procedure using 5,15-di-p-bromophenylporphyrin (31.0 mg, 0.05 mmol), Pd(OAc)$_2$ (1.12 mg, 0.005 mmol), ligand 3 (3.8 mg, 0.01 mmol), NaOtBu (38.22 mg, 0.4 mmol), p-anisidine (49.3 mg, 0.4 mmol) and THF, the reaction proceeded at 100° C. for 48 h. After workup with general procedure, the title compound was obtained (32.6 mg, 93%). $^1$H NMR (DMSO-d$_6$, 300 MHz) δ 10.56 (s, meso-2H), 9.62 (d, J=4.2 Hz, β-4H), 9.15 (d, J=4.8 Hz, β-4H), 8.44 (s, 2H), 8.07 (d, J=7.8 Hz, 4H), 7.37 (d, J=9.0 Hz, 4H), 7.41 (d, J=8.7 Hz, 4H), 7.02 (d, J=8.4 Hz, 4H), 3.78 (s, 6H), −3.09 (s, 2H). $^{13}$C NMR (DMSO-d$_6$, 75 MHz) δ 154.3, 147.0, 145.2, 144.4, 136.1, 135.7, 134.7, 134.6, 132.3, 129.9, 121.4, 119.3, 114.7, 113.3, 55.3. UV-vis (λ$_{max}$, m) 418, 510, 552, 583, 640. HRMS-EI ([M+1]$^+$): calc'd for, C$_{46}$H$_{37}$N$_6$O$_2$, 705.2978; found 705.3018.

Example 29

Synthesis of 5,15-di-p-[N-(4-methoxyphenyl)amino] phenylporphyrin (Zn II) (Table 2, entry 3, B)

The general procedure using 5,15-di-p-bromophenylporphyrin (Zn II)(34.5 mg, 0.05 mmol), Pd(OAc)$_2$ (1.12 mg, 0.005 mmol), ligand 8 (3.98 mg, 0.01 mmol), NaOtBu (38.22 mg, 0.4 mmol), p-anisidine (49.3 mg, 0.4 mmol) and THF, the reaction proceeded at 100° C. for 48 h. After workup with general procedure, the title compound was obtained (26 mg, 68%). $^1$H NMR (DMSO-d$_6$, 300 MHz) δ 10.29 (s, meso-2H), 9.47 (d, J=4.5 Hz, β-4H), 9.07 (d, J=4.2 Hz, β-4H), 8.36 (s, 2H), 8.02 (d, J=8.1 Hz, 4H), 7.39 (d, J=8.1 Hz, 4H), 7.37 (d, J=8.1 Hz, 4H), 7.01 (d, J=8.1 Hz, 4H), 3.78 (s, 6H). $^{13}$C NMR (DMSO-d$_6$, 75 MHz) δ 154.1, 149.8, 148.7, 144.6, 136.1, 135.7, 134.7, 132.3, 131.9, 131.8, 121.0, 119.5, 114.7, 113.0, 105.8, 55.3. UV-vis (λ$_{max}$, nm) 419, 545, 585.

Example 30

Synthesis of 5,15-di-p-(N-benzylamino) phenylporphyrin (Zn II) (Table 2, entry 4, B)

The general procedure using 5,15-di-p-bromophenylporphyrin (Zn II)(34.2 mg, 0.05 mmol), Pd(OAc)$_2$ (1.12 mg, 0.005 mmol), ligand 8 (3.98 mg, 0.01 mmol), NaOtBu (38.22 mg, 0.4 mmol), benzylamine (43.7 μl, 0.4 mmol) and THF, the reaction proceeded at 100° C. for 48 h. After workup with general procedure, the title compound was obtained (30.7 mg, 83%). $^1$H NMR (CDCl$_3$, 300 MHz) δ 10.17 (s, meso-2H), 9.35 (d, J=4.2 Hz, β-4H), 9.17 (d, J=4.8 Hz, β-4H), 8.04 (d, J=7.2 Hz, 4H), 7.58 (d, J=7.5 Hz, 4H), 7.35–7.49 (m, 6H), 7.02 (d, J=7.5 Hz, 4H), 5.5 (s, 2H). UV-vis (λ$_{max}$, nm) 419, 543, 584.

Example 31

Synthesis of 5,15-di-p-[N-(4-methylpyridyl)amino] phenylporphyrin (Table 2, entry 5, A)

The general procedure using 5,15-di-p-bromophenylporphyrin (31.0 mg, 0.05 mmol), Pd(OAc)$_2$ (1.12 mg, 0.005 mmol), (±) BINAP (6.2 mg, 0.01 mmol, 9), NaOtBu (38.22 mg, 0.4 mmol), 4-aminomethylpyridine (41 μl, 0.4 mmol) and THF, the reaction proceeded at 100° C. for 48 h. After workup with general procedure, the title compound was obtained (29.6 mg, 88%). Different yield was observed by using other conditions (table 1). $^1$H NMR (DMSO-d$_6$, 300 MHz) δ 10.52 (s, meso-2H), 9.58 (d, J=4.5 Hz, β-4H), 9.07 (d, J=4.2 Hz, β-4H), 8.63 (d, J=5.7 Hz, 4H), 7.98 (d, J=8.4 Hz, 4H), 7.58 (d, J=5.7 Hz, 4H), 7.05 (d, J=8.7 Hz, 4H), 6.97 (t, 2H), 4.61 (d, J=5.7, 4H), −3.10 (s, 2H). $^{13}$C NMR (DMSO-d$_6$, 75 MHz) δ 149.8, 148.2, 147.1, 144.6, 136.0, 134.6, 134.4, 134.3, 132.2, 130.8, 128.1, 122.5, 111.4, 105.4, 45.6. UV-vis (λ$_{max}$, nm) 416, 508, 548, 581, 638.

Example 32

Synthesis of 5,15-di-p-[N-(o-methylphenyl)amino] phenylporphyrin (Table 2, entry 6, A)

The general procedure using 5,15-di-p-bromophenylporphyrin (31.0 mg, 0.05 mmol), Pd(OAc)$_2$ (1.12 mg, 0.005 mmol), ligand 3 (3.8 mg, 0.01 mmol), NaOtBu (38.22 mg, 0.4 mmol), o-toluidine (43 μl, 0.4 mmol) and THF, the reaction proceeded at 100° C. for 48 h. After workup with general procedure, the title compound was obtained (29.1 mg, 87%). $^1$H NMR (DMSO-d$_6$, 300 MHz) δ 10.56 (s, meso-2H), 9.62 (d, J=4.8 Hz, β-4H), 9.16 (d, J=4.8 Hz, β-4H), 8.08 (d, J=8.7 Hz, 4H), 7.98 (s, 2H), 7.59 (d, J=7.5 Hz, 2H), 7.38 (d, J=8.7 Hz, 4H), 7.27–7.38 (m, 4H), 7.04 (m, 2H), 2.44 (s, 6H), −3.10 (s, 2H). $^{13}$C NMR (DMSO-d$_6$, 75 MHz) δ 147.5, 144.9, 142.6, 140.9, 135.9, 131.4, 131.2, 131.0, 128.9, 126.9, 122.6, 119.6, 115.5, 105.1, 18.0. UV-vis (λ$_{max}$, nm) 419, 510, 552, 583, 640. HRMS-EI ([M+1]$^+$): calc'd for, C$_{46}$H$_{37}$N$_6$, 673.3080; found 673.3107.

Example 33

Synthesis of 5,15-di-p-[N-(o-methylphenyl)amino] phenylporphyrin(Zn(II)) (Table 2, entry 6, B)

The general procedure using 5,15-di-p-bromophenylporphyrin(Zn(II)) (34.2 mg, 0.05 mmol), Pd(OAc)$_2$ (1.12 mg, 0.005 mmol), ligand 3 (3.8 mg, 0.01 mmol), NaOtBu (38.22 mg, 0.4 mmol), o-toluidine (43 μl, 0.4 mmol) and THF, the reaction proceeded at 100° C. for 48 h. After workup with general procedure, the title compound (29.1 mg, 87%) was obtained. $^1$H NMR (DMSO-d$_6$, 300 MHz) δ 10.23 (s, meso-2H), 9.39 (d, J=4.8 Hz, β-4H), 9.20 (d, J=4.8 Hz, β-4H), 8.11 (d, J=8.1 Hz, 4H), 7.63 (d, J=7.5 Hz, 2H), 7.36 (d, J=8.4 Hz, 4H), 7.27–7.35 (m, 4H), 7.04 (dd, J=7.8 Hz 2H), 5.76 (s, 2H), 2.48 (s, 6H). $^{13}$C NMR (CDCl$_3$, 75 MHz) δ 150.3, 149.3, 139.7, 135.8, 132.3, 131.4, 131.1, 122.2, 115.4, 105.8, 18.2. UV-vis (λ$_{max}$, nm) 421, 542, 583. HRMS-EI ([M-Zn+1]$^+$): calc'd for, C$_{46}$H$_{35}$N$_6$, 673.3080; found 673.3075.

Example 34

Synthesis of 5,15-di-n-butylaminophenylporphyrin (Table 1, entry 7, A)

The general procedure using 5,15-di-p-bromophenylporphyrin (31.0 mg, 0.05 mmol), Pd(OAc)$_2$ (1.12 mg, 0.005 mmol), ligand 3 (3.78 mg, 0.01 mmol), NaOtBu (38.22 mg, 0.4 mmol), n-butylamine (40 μl, 0.4 mmol) and THF (4–6 mL), the reaction proceeded at 100° C. for 48 h. After workup with general procedure, the title compound (27.7 mg, 92%) was obtained. By using other ligand or other condition, the same product with different yield was obtained (table 1, entry 7). $^1$H NMR (CDCl$_3$, 300 MHz) δ 10.25 (s, meso-2H), 9.35 (d, J=4.6 Hz, β-4H), 9.16 (d, J=4.5 Hz, β-4H), 8.06 (d, J=8.4 Hz, 4H), 7.03 (d, J=8.4 Hz, 4H), 3.40 (t, J=6.6, 7.2 Hz, 4H), 1.83 (m, 4H), 1.59 (m, 4H), 1.08 (m, 6H), −3.00 (s, 2H). $^{13}$C NMR (CDCl$_3$, 75 MHz) δ 148.1, 147.8, 144.8, 136.1, 131.2, 131.1, 130.0, 119.7, 111.3, 104.9, 44.9, 31.8, 20.5, 14.1. UV-vis (λ$_{max}$, nm) 419, 511, 553, 586, 641. HRMS-EI ([M+1]$^+$): calc'd for C$_{40}$H$_{41}$N$_6$, 605.3393; found 605.3395.

Example 35

Synthesis of 5,15-di-n-butylaminophenylporphyrin (Zn II) (Table 2, entry 7, B)

The general procedure using 5,15-di-p-bromophenylporphyrin (Zn II) (34.2 mg, 0.05 mmol), Pd(OAc)$_2$ (1.12 mg, 0.005 mmol), ligand 8 (3.98 mg, 0.01 mmol), NaOtBu (38.22 mg, 0.4 mmol), n-butylamine (40 μl, 0.4 mmol) and THF (4–6 mL), the reaction proceeded at 100° C. for 48 h. After workup with general procedure, the title compound (31.1 mg, 93%) was obtained. $^1$H NMR (DMSO-d$_6$, 300 MHz) δ 10.26 (s, meso-2H), 9.44 (d, J=4.8 Hz, β-4H), 9.04 (d, J=4.8 Hz, β4H), 7.92 (d, J=8.1 Hz, 4H), 7.01 (d, J=8.1 Hz, 4H), 6.04 (t, 2H), 3.28 (m, 4H), 1.76 (m, 4H), 1.55 (m, 4H), 1.05 (m, 6H). $^{13}$C NMR (DMSO-d$_6$, 75 MHz) δ 149.9, 148.5, 135.6, 134.5, 134.3, 131.6, 129.5, 110.4, 42.8, 31.2, 20.1, 14.0. UV-vis (λ$_{max}$, nm419, 545, 586. HRMS-EI ([(M-Zn)+1]$^+$): calc'd for C$_{40}$H$_{41}$N$_6$, 605.3393; found 605.3360.

Example 36

Synthesis of 5,15-di-n-hexylaminophenylporphyrin (Table 2, entry 8, A)

The general procedure using 5,15-di-p-bromophenylporphyrin (31.0 mg, 0.05 mmol), Pd(OAc)$_2$ (1.12 mg, 0.005 mmol), ligand 3 (3.78 mg, 0.01 mmol), NaOtBu (38.22 mg, 0.4 mmol), n-hexylamine (52.8 μl, 0.4 mmol) and THF (4–6 mL), the reaction proceeded at 100° C. for 48 h. After workup with general procedure, the title compound (29.7 mg, 90%) was obtained. $^1$H NMR (CDCl$_3$, 300 MHz) δ 10.25 (s, meso-2H), 9.35 (d, J=4.8 Hz, β-4H), 9.16 (d, J=4.2 Hz, β-4H), 8.05 (d, J=8.4 Hz, 4H), 7.03 (d, J=8.4 Hz, 4H), 4.05 (br, s, 2H), 3.40 (t, J=7.2 Hz, 4H), 1.84 (m, 4H), 1.54 (m, 4H), 1.43 (m, 4H), 0.97 (m, 6H), −3.00 (s, 2H). $^{13}$C NMR (CDCl$_3$, 75 MHz) δ 148.1, 147.8, 144.8, 136.1, 131.2, 131.1, 130.0, 119.7, 111.4, 104.9, 44.3, 31.8, 29.7, 27.0, 22.7, 14.1. UV-vis (λ$_{max}$, nm) 421, 509, 549, 583, 638.

Example 37

5,15-di-n-hexylaminophenylporphyrin (Zn II) (Table 2, entry 8, B)

The general procedure using 5,15-di-p-bromophenylporphyrin (Zn II) (34.2 mg, 0.05 mmol), Pd(OAc)$_2$ (1.12 mg, 0.005 mmol), ligand 7 (5.78 mg, 0.01 mmol), NaOtBu (38.22 mg, 0.4 mmol), n-hexylamine (52.8 μl, 0.4 mmol) and THF (4–6 mL), the reaction proceeded at 100° C. for 48 h. After workup with general procedure, the title compound (17 mg, 53%) was obtained. $^1$H NMR (CDCl$_3$, 300 MHz) δ 10.22 (s, meso-2H), 9.38 (d, J=4.8 Hz, β-4H), 9.18 (d, J=4.2 Hz, β-4H), 7.95 (d, J=8.1 Hz, 4H), 6.70 (d, J=8.1 Hz, 4H), 3.44 (m, 4H), 2.95 (m, 4H), 1.76 (m, 4H), 1.61 (m, 4H), 1.36 (m, 8H), 0.94 (m, 6H). $^{13}$C NMR (DMSO-d$_6$, 75 MHz) δ 150.5, 149.2, 139.4, 135.4, 132.5, 131.1, 111.4, 104.9, 44.1, 31.5, 28.0, 26.6, 22.7, 14.1. UV-vis (λ$_{max}$, nm) 419, 543, 584.

Example 38

5,15-di-p-(N-methyl, N-phenylamino)phenylporphyrin (Table 2, entry 9, A)

The general procedure using 5,15-di-p-bromophenylporphyrin (31.0 mg, 0.05 mmol), Pd(OAc)$_2$ (1.12 mg, 0.005 mmol), ligand 3 (3.78 mg, 0.01 mmol), NaOtBu (38.22 mg, 0.4 mmol), N-methylaniline (43.7 μl, 0.4 mmol) and THF (4–6 mL), the reaction proceeded at 100° C. for 48 h. After workup with general procedure, the title compound (29.5 mg, 88%) was obtained. $^1$H NMR (CDCl$_3$, 300 MHz) δ 10.28 (s, meso-2H), 9.39 (d, J=4.8 Hz, β-4H), 9.20 (d, J=4.8 Hz, β-4H), 8.14 (d, J=8.7 Hz, 4H), 7.37–7.50 (m, 12H), 7.13 (dd, J=2.1, 6.6 Hz, 2H), 3.62 (s, 6H), −3.02 (s, 2H). $^{13}$C NMR (CDCl$_3$, 75 MHz) δ 148.9, 148.5, 147.6, 144.9, 135.8, 133.0, 131.4, 131.1, 129.6, 122.8, 122.7, 119.2, 116.9, 105.1, 40.6. UV-vis (λ$_{max}$, nm) 413, 510, 552, 583, 640. HRMS-EI ([M]$^+$): calc'd for C$_{46}$H$_{36}$N$_6$, 672.3001; found 672.3010.

Example 39

Synthesis of 5,15-di-p-(N-methyl, N-phenylamino)phenylporphyrin (Zn II) (Table 2, entry 9, B)

The general procedure using 5,15-di-p-bromophenylporphyrin (Zn II) (34.2 mg, 0.05 mmol), Pd(OAc)$_2$ (1.12 mg, 0.005 mmol), ligand 3 (3.78 mg, 0.01 mmol), NaOtBu (38.22 mg, 0.4 mmol), N-methylaniline (43.7 μl, 0.4 mmol) and THF (4–6 mL), the reaction proceeded at 100° C. for 48 h. After workup with general procedure, the title compound (27 mg, 73%) was obtained. $^1$H NMR (CDCl$_3$, 300 MHz) δ 10.24 (s, meso-2H), 9.39 (d, J=4.2 Hz, β-4H), 9.22 (d, J=4.8 Hz, β-4H), 8.12 (d, J=8.1 Hz, 4H), 7.37–7.49 (m, 12H), 7.13 (m, 2H), 3.63 (s, 6H). $^{13}$C NMR (CDCl$_3$, 75 MHz) δ 150.4, 149.2, 148.3, 135.6, 134.5, 132.6, 131.5, 129.5, 122.4, 122.2, 117.0, 106.0, 40.6. UV-vis (λ$_{max}$, nm) 413, 544, 587. HRMS-EI ([M-Zn+1]$^+$): calc'd for C$_{46}$H$_{35}$N$_6$, 673.3080; found 673.3104.

Example 40

Synthesis of 5,15-di-p-diphenylaminophenylporphyrin (Table 2, entry 10, A)

The general procedure using 5,15-di-p-bromophenylporphyrin (31.0 mg, 0.05 mmol), Pd(OAc)$_2$ (1.12 mg, 0.005 mmol), ligand 3 (3.78 mg, 0.01 mmol), NaOtBu (38.22 mg, 0.4 mmol), diphenylamine (67.7 mg, 0.4 mmol) and THF (4–6 mL), the reaction proceeded at 100° C. for 48 h. After workup with general procedure, the title compound (32.4 mg, 81%) was obtained. $^1$H NMR (CDCl$_3$, 300 MHz) δ 10.28 (s, meso-2H), 9.39 (d, J=4.8 Hz, β-4H), 9.20 (d, J=4.8 Hz, β-4H), 8.14 (d, J=8.7 Hz, 4H), 7.37–7.50 (m, 12H), 7.13 (dd, J=2.1, 6.6 Hz, 2H), 3.62 (s, 6H), −3.04 (s, 2H). $^{13}$C NMR (CDCl$_3$, 75 MHz) δ 147.8, 135.8, 131.5, 131.0, 129.5, 124.9, 123.3, 121.6, 105.2. UV-vis (λ$_{max}$, nm) 410, 510, 552, 583, 640. HRMS-EI ([M+1]$^+$): calc'd for C$_{56}$H$_{41}$N$_6$, 797.3393; found 797.3398.

Example 41

Synthesis of 5,15-di-p-diphenylaminophenylporphyrin (Zn II) (Table 2, entry 10, B)

The general procedure using 5,15-di-p-bromophenylporphyrin (Zn II) (34.2 mg, 0.05 mmol), Pd(OAc)$_2$ (1.12 mg, 0.005 mmol), ligand 8 (3.98 mg, 0.01 mmol), NaOtBu (38.22 mg, 0.4 mmol), diphenylamine (67.7 mg, 0.4 mmol) and THF (4–6 mL), the reaction proceeded at 100° C. for 48 h. After workup with general procedure, the title compound (24.5 mg, 57%) was obtained. $^1$H NMR (DMSO-d$_6$, 300 MHz) δ 10.35 (s, meso-2H), 9.52 (d, J=4.8 Hz, β-4H), 9.08 (d, J=4.5 Hz, β-4H), 8.12 (d, J=8.1 Hz, 4H), 7.37–7.51 (m, 12H), 7.17 (m, 4H). $^{13}$C NMR (DMSO-d$_6$, 75 MHz) δ 149.4, 148.9, 147.4, 146.6, 136.6, 135.6, 132.1, 129.9, 124.5, 123.4, 121.1, 118.8, 116.7, 106.1. UV-vis (λ$_{max}$, nm) 416, 543, 584. HRMS-EI ([M-Zn+1]$^+$): calc'd for C$_{56}$H$_{41}$N$_6$Zn, 797.3393; found 797.3408.

Example 42

Synthesis of 5,15-di-p-benzophenone iminophenylporphyrin (Table 2, entry 11, A)

The general procedure using 5,15-di-p-bromophenylporphyrin (31.0 mg, 0.05 mmol), Pd$_2$(dba)$_3$ (4.58 mg, 0.005 mmol), ligand 1 (2.98 mg, 0.01 mmol), NaOtBu (38.22 mg, 0.4 mmol), benzophenone imine (67.1 μl, 0.4 mmol) and THF (4–6 mL), the reaction proceeded at 100° C. for 48 h. After workup with general procedure, the title compound (21.4 mg, 81%) was obtained. $^1$H NMR (CDCl$_3$, 300 MHz) δ 10.27 (s, meso-2H), 9.36 (d, J=4.8 Hz, β-4H), 9.95 (d, J=4.8 Hz, β-4H), 8.0 (d, J=7.5 Hz, 4H), 7.95 (d, J=8.7 Hz, 4H), 7.52 (m, 12H), 7.43 (m, 4H), 7.13 (d, J=7.5 Hz, 4H), −3.18 (s, 2H). $^{13}$C NMR (CDCl$_3$, 75 MHz) δ 142.9, 142.6, 135.9, 131.5, 131.0, 129.6, 121.6, 118.6, 115.7, 105.1. UV-vis (λ$_{max}$, nm) 412, 506, 541, 578, 634. HRMS-EI ([M+1]$^+$): calc'd for C$_{58}$H$_{41}$N$_6$, 821.3393; found 821.3370.

Example 43

Synthesis of 5,15-di-p-morpholinophenylporphyrin (Table 2, entry 11, A)

The general procedure using 5,15-di-p-bromophenylporphyrin (31.0 mg, 0.05 mmol), Pd(OAc)$_2$ (1.12 mg, 0.005 mmol), ligand 8 (3.98 mg, 0.01 mmol), Cs$_2$CO$_3$ (130.33 mg, 0.4 mmol), morpholine (35 μl, 0.4 mmol) and THF (4–6 mL), the reaction proceeded at 100° C. for 48 h. After workup with general procedure, the title compound (25 mg, 76%) was obtained.

Example 44

Synthesis of Tetrakis-p-(N-phenylamino) phenylporphyrin (Table 3, entry 1)

The general procedure using tetrakis-p-bromophenylporphyrin (46.5 mg, 0.05 mmol), Pd(OAc)$_2$ (2.24 mg, 0.01 mmol), (±) BINAP (12.4 mg, 0.02 mmol, 9), NaOtBu (76.44 mg, 0.8 mmol), aniline (73 μl, 0.8 mmol) and THF (4–6 mL), the reaction proceeded at 100° C. for 72 h. After workup with general procedure, the title compound (44.6 mg, 91%) was obtained. $^1$H NMR (CDCl$_3$, 300 MHz) $^1$H NMR (CDCl$_3$, 300 MHz) δ 8.95 (s, β-8H), 8.08 (d, J=8.1 Hz, 8H), 7.34–7.42 (m, 24H), 7.04 (t, J=6.6, 7.2 Hz, 4H), 6.05 (s, 4H), −2.66 (s, 2H). $^{13}$C NMR (CDCl$_3$, 75 MHz) δ 142.9, 142.7, 135.7, 134.6, 129.5, 121.5, 119.9, 118.5, 115.3. UV-vis (λ$_{max}$, nm) 433, 524, 566, 657. HRMS-EI ([M+1]$^+$): calc'd for C$_{68}$H$_{51}$N$_8$, 979.4237; found 979.4218.

Example 45

Synthesis of Tetrakis-p-(n-butylamino) phenylporphyrin (Table 3, entry 2)

The general procedure using tetrakis-p-bromophenylporphyrin (46.5 mg, 0.05 mmol), Pd(OAc)$_2$ (2.24 mg, 0.01 mmol), ligand 8 (7.96 mg, 0.02 mmol), NaOtBu (76.44 mg, 0.8 mmol), n-butylamine (80 μl, 0.8 mmol) and THF (4–6 mL), the reaction proceeded at 100° C. for 72 h. After workup with general procedure, the title compound (38.5 mg, 86%) was obtained. $^1$H NMR (CDCl$_3$, 300 MHz) δ 8.91 (s, β-8H), 8.01 (d, J=8.1 Hz, 8H), 6.95 (d, J=8.1 Hz, 8H), 3.95 (s, 4H), 3.60 (t, J=7.2, 8.4 Hz, 8H), 1.79 (m, 8H), 1.59 (m, 8H), 1.06 (t, J=6.9, 7.2 Hz, 12H), −2.64 (s, 2H). $^{13}$C NMR (CDCl$_3$, 75 MHz) δ 147.9, 135.8, 131.3, 120.3, 110.9, 43.9, 31.9, 20.5, 14.0. UV-vis (λ$_{max}$, nm) 434, 527, 571, 661. HRMS-EI ([M+1]$^+$): calc'd for C$_{60}$H$_{67}$N$_8$, 899.5489; found 899.5507.

Example 46

Synthesis of Tetrakis-β-(N-methyl, N-phenylamino) phenylporphyrin (Table 3, entry 3)

The general procedure using tetrakis-p-bromophenylporphyrin (46.5 mg, 0.05 mmol), Pd(OAc)$_2$ (2.24 mg, 0.01 mmol), (±) BINAP (12.4 mg, 0.02 mmol, 9), NaOtBu (76.44 mg, 0.8 mmol), N-methylaniline (87.4 μl, 0.8 mmol) and THF (4–6 mL), the reaction proceeded at 100° C. for 72 h. After workup with general procedure, the title compound (42.4 mg, 82%) was obtained. $^1$H NMR (CDCl$_3$, 300 MHz) δ 8.78 (s, β-8H), 7.92 (d, J=7.8 Hz, 8H), 7.21–7.30 (m, 16H), 7.16 (d, J=8.1 Hz, 8H), 7.05 (s, 2H), 6.95 (t, 4H), 3.42 (s, 12H), −2.81 (s, 2H). $^{13}$C NMR (CDCl$_3$, 75 MHz) 6148.9, 148.4, 135.6, 134.1, 129.5, 122.7, 122.6, 122.5, 120.1, 116.6, 116.5, 40.5. UV-vis (λ$_{max}$, nm) 435, 525, 567, 657. HRMS-EI ([M+1]$^+$): Calc'd for C$_{72}$H$_{59}$N$_8$, 1035.4863; found 1035.4836.

Example 47

Synthesis of Tetrakis-p-(diphenylamino) phenylporphyrin (Table 3, entry 4)

The general procedure using tetrakis-p-bromophenylporphyrin (46.5 mg, 0.05 mmol), Pd(OAc)$_2$ (2.24 mg, 0.01 mmol), ligand 3 (7.56 mg, 0.02 mmol), NaOtBu (76.44 mg, 0.8 mmol), diphenylamine (135.4 mg, 0.8 mmol) and THF (4–6 mL), the reaction proceeded at 100° C. for 72 h. After workup with general procedure, the title compound (52.2 mg, 81%) was obtained. $^1$H NMR (CDCl$_3$, 300 MHz) δ 9.02 (s, β-8H), 8.12 (d, J=8.7 Hz, 8H), 7.47 (d, J=8.4 Hz, 8H), 7.43 (s, 16H), 7.41 (m, 4H), 7.15 (s, 8H), −2.66 (s, 2H). $^{13}$C NMR (CDCl$_3$, 75 MHz) δ 147.8, 147.4, 135.9, 135.7, 129.5, 124.8, 123.3, 121.3, 119.9, 117.7. UV-vis (λ$_{max}$, nm) 439, 526, 570, 659. HRMS-EI ([M+1]$^+$): calc'd for C$_{92}$H$_{67}$N$_8$, 1283.5489; found 1283.5478.

Example 48 through 58 relate to methods for synthesizing meso-substituted phenoxyporphyrins, and the phenoxyporphyrin compounds so made, according to the present invention.

Example 48

General Procedure

All reactions were carried out under a nitrogen atmosphere in oven-dried glassware using standard Schlenk techniques. Toluene was distilled under nitrogen from sodium benzophenone ketyl. Deuterated solvents were purchased from Cambridge Isotope Laboratories and were used as supplied. All other solvents were of liquid chromatography grade, which were purchased from Fisher Scientific and used as supplied. Phenols were purchased from Acros Organics or Aldrich Chemical Co. and used without further purification. [5-bromo-10,20-diphenylporphyrino]zinc(II) and [5,15-dibromo-10,20-diphenylporphyrino]zinc(II) were synthesized according to the literature. Phosphine ligands notably, bis(2-diphenylphosphinophenyl)ether (DPEphos), were purchased from Strem along with the metal precursors; palladium(II) acetate and tris(dibenzylideneacetone) dipalladium(0). Cesium carbonate was obtained as a gift from Chemetall Chemical Products, Inc. Proton and carbon nuclear magnetic resonance spectra ($^1$H NMR and $^{13}$C NMR) were recorded on a Varian Mercury 300 spectrometer and referenced with respect to residual solvent. Infrared spectra were obtained using a Bomen B100 Series FT-IR spectrometer. Samples were prepared as films on a NaCl plate by evaporating THF solutions. UV-Vis spectra were obtained using a Hewlett-Packard 8452A diode array spectrophotometer. High-resolution mass spectroscopy was performed by the Mass Spectrometry Center located in the Chemistry Department of the University of Tennessee on a VG Analytical hybrid high performance ZAB-EQ (B-E-Q geometry) instrument using electron impact (EI) ionization technique with a 70 eV electron beam. Thin layer chromatography was carried out on E. Merck Silica Gel 60 F-254 TLC plates.

Example 49

General Procedures for Catalytic C—O Coupling of Bromoporphyrin

The bromoporphyrin, palladium precursor, phosphine ligand and base were placed in an oven-dried, resealable Schlenk tube. The tube was sealed with a Teflon screw cap, evacuated, and backfilled with nitrogen. The screw cap was replaced with a rubber septum; the phenol was then added via syringe, followed by solvent. The tube was purged with nitrogen for 2 min, and then the septum was replaced with the Teflon screw cap. The tube was sealed, and its contents were placed in a heated oil-bath with constant stirring until the starting bromoporphyrin had been completely consumed as indicated by TLC analysis. The resulting mixture was cooled to room temperature, taken up in ethyl acetate (60 mL) and transferred to a separatory funnel. The mixture was then washed with water (×2), dried over anhydrous sodium sulfate, filtered and dried in vacuo. The crude product was then purified.

Example 50

Synthesis of 5-phenoxy-10,20-diphenylporphinato zinc(II)

The general procedure was used to couple 5-bromo-10, 20-diphenylporphinato zinc(II) (30 mg, 0.05 mmol) with phenol (17 mg, 0.018 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 23 hours. Isolated via flash chromatography (silica gel, THF:hexanes (v)=1:8 as a red solid (24 mg, 80%). $^1$H NMR (300 MHz, CDCl$_3$): δ 10.13 (s, 1H), 9.39 (d, J=4.5 Hz, 2H), 9.31 (d, J=4.8 Hz, 2H), 9.09 (d, J=4.5 Hz, 2H), 8.92 (d, J=4.8 Hz, 2H), 8.19 (m, 4H), 7.74 (m, 6H), 7.23 (m, 2H), 7.02 (m, 3H). $^{13}$C NMR (75 MHz, CDCl$_3$): δ 165.9, 150.3, 150.1, 149.7, 145.8, 142.3, 134.5, 132.9, 132.2, 131.8, 129.6, 128.0, 127.5, 126.6, 121.5, 120.7, 116.6, 107.7, 105.6. UV-vis (CHCl$_3$, $\lambda_{max}$, nm): 218, 418. IR (film, cm$^{-1}$): 3609, 3583, 3047, 2362, 1591, 1544, 1486, 1440, 1384, 1361, 1319, 1295, 1214, 1163, 1147, 1062, 996, 851, 790, 750, 721, 701. HRMS-EI ([M]$^+$): C$_{38}$H$_{24}$N$_4$OZn, 616.124; found: 616.125.

Example 51

Synthesis of 5-(4-methoxyphenoxy)-10,20-diphenylporphinato zinc(II)

The general procedure was used to couple 5-bromo-10, 20-diphenylporphinato zinc(II) (30 mg, 0.05 mmol) with 4-methoxyphenol (22 mg, 0.18 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 17 hours. Isolated via flash chromatography (silica gel, THF:hexanes (v)=1:8 as a red solid (29.9 mg, 93%). $^1$H NMR (300 MHz, CDCl$_3$): δ 10.02 (s, 1H), 9.35 (d, J=4.2 Hz, 2H), 9.24 (d, J=3.9 Hz, 2H), 8.98 (d, J=4.2 Hz, 2H), 8.8 (d, J=3.9 Hz, 2H), 8.18 (m, 4H), 7.75 (m, 6H), 6.92 (d, J=8.4 Hz, 2H), 6.67 (d, J=8.4 Hz, 2H), 3.60 (S, 3H). $^{13}$C NMR (75 MHz, CDCl$_3$): δ 160.8, 153.9, 150.2, 150.0, 149.5, 145.9, 142.6, 134.6, 132.7, 132.1, 132.0, 131.6, 127.9, 127.4, 126.5, 120.4, 117.1, 114.6, 105.2, 55.6. UV-vis (CHCl$_3$, $\lambda_{max}$, nm): 418, 548. IR (film, cm$^{-1}$): 3291, 3054, 2973, 2954, 2877, 2833, 2738, 1808, 1721, 1595, 1538, 1502, 1459, 1440, 1385, 1360, 1322, 1294, 1243, 1147, 1103, 1061, 1037, 994, 881, 846, 827, 793, 751, 724, 701. HRMS-EI ([M]$^+$): C$_{39}$H$_{26}$N$_4$O$_2$Zn, 646.135; found: 646.137.

Example 52

Synthesis of 5-(4-t-butylphenoxy)-10,20-diphenylporphinato zinc(II)

The general procedure was used to couple 5-bromo-10, 20-diphenylporphinato zinc(II) (30 mg, 0.05 mmol) with 4-t-butylphenol (27 mg, 0.18 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 18 hours. Isolated via flash chromatography (silica gel, THF:hexanes (v)=1:8 as a red solid (23.8 mg, 73%). $^1$H NMR (300 MHz, CDCl$_3$): δ 10.16 (s, 1H), 9.45 (d, J=4.8 Hz, 2H), 9.34 (d, J=4.2 Hz, 2H), 9.06 (d, J=4.5 Hz, 2H), 8.93 (d, J=4.8 Hz, 2H), 8.22 (m, 4H), 7.77 (m, 6H), 7.24 (d, J=9.9 Hz, 2H), 6.96 (d, J=8.7 Hz, 2H), 1.26 (S, 9H). $^{13}$C NMR (75 MHz, CDCl$_3$): δ 164.0, 159.9, 150.4, 150.1, 149.7, 146.0, 144.1, 142.4, 134.5, 132.9, 132.1, 131.7, 128.1, 127.5, 126.7, 126.3, 120.66, 115.9, 105.5, 31.5, 29.7. UV-vis (CHCl$_3$, $\lambda_{max}$, nm): 418, 548. IR (film, cm$^{-1}$): 3297, 3054, 3027, 2961, 2872, 1806, 1599, 1542, 1505, 1488, 1460, 1386, 1362, 1322, 1295, 1266, 1220, 1173, 1150, 1110, 1062, 1041, 995, 883, 846, 832, 792, 750, 723, 701. HRMS-EI ([M]$^+$): C$_{42}$H$_{32}$N$_4$OZn, 672.187; found: 672.186.

Example 53

Synthesis of 5-(4-fluorophenoxy)-10,20-diphenylporphinato zinc(II)

The general procedure was used to couple 5-bromo-10, 20-diphenylporphinato zinc(II) (30 mg, 0.05 mmol) with 4-fluorophenol (20 mg, 0.18 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 17 hours. Isolated via flash chromatography (silica gel, THF:hexanes (v)=1:8 as a red solid (25.4 mg, 78%). $^1$H NMR (300 MHz, CDCl$_3$): δ 10.10 (s, 1H), 9.35 (d, J=4.5 Hz, 2H), 9.29 (d, J=4.2 Hz, 2H), 9.02 (d, J=4.8 Hz, 2H), 8.91 (d, J=4.8 Hz, 2H), 8.19 (m, 4H), 7.76 (m, 6H), 6.93 (m, 4H). $^{13}$C NMR (75 MHz, CDCl$_3$): δ 150.4, 150.2, 149.70, 145.4, 134.5, 132.9, 132.2, 131.8, 127.7, 127.5, 126.6, 120.6, 117.4, 117.2, 116.1, 115.8, 105.6. UV-vis (CHCl$_3$, λ$_{max}$, nm): 418, 546. IR (film, cm$^{-1}$): 3273, 3101, 3073, 3054, 3023, 2974, 2933, 2875, 2740, 2951, 2582, 2552, 1807, 1719, 1597, 1541, 1520, 1498, 1459, 1440, 1386, 1360, 1322, 1295, 1260, 1195, 1145, 1091, 1062, 1041, 995, 885, 847, 832, 793, 751, 724, 701. HRMS-EI ([M]$^+$): C$_{38}$H$_{23}$N$_4$OFZn, 634.115; found: 634.113.

Example 54

Synthesis of 5-(2-isopropylphenoxy)-10,20-diphenylporphinato zinc(II)

The general procedure was used to couple 5-bromo-10,20-diphenylporphinato zinc(II) (30 mg, 0.05 mmol) with 2-isopropylphenol (25 μL, 0.018 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 17 hours. Isolated via flash chromatography (silica gel, THF:hexanes (v)=1:8 as a red solid (23 mg, 72%). $^1$H NMR (300 MHz, CDCl$_3$): δ 10.05 (s, 1H), 9.33 (d, J=4.8 Hz, 2H), 9.26 (d, J=4.5 Hz, 2H), 9.01 (d, J=4.8 Hz, 2H), 8.90 (d, J=4.5 Hz, 2H), 8.19 (m, 4H), 7.75 (m, 6H), 7.60 (d, J=7.8 Hz, 1H), 6.96 (t, J=7.5 Hz, 1H), 6.67 (t, J=7.2 Hz, 1H), 6.02 (d, J=8.1 Hz, 1H), 4.40 (m, 1H), 1.82 (d, J=6.9 Hz, 6H). $^{13}$C NMR (75 MHz, CDCl$_3$): δ 163.86, 150.3, 150.0, 149.6, 145.8, 142.5, 135.8, 134.5, 132.8, 132.1, 131.6, 127.9, 127.4, 126.6, 126.5, 121.3, 120.4, 116.4, 105.2, 28.0, 23.3. UV-vis (CHCl$_3$, λ$_{max}$, nm): 418, 546. IR (film, cm$^{-1}$): 3293, 3055, 3026, 2961, 2873, 1805, 1596, 1542, 1483, 1441, 1385, 1360, 1322, 1294, 1261, 1218, 1191, 1154, 1061, 1039, 994, 885, 847, 824, 793, 750, 723, 701. HRMS-EI ([M]$^+$): C$_{41}$H$_{30}$N$_4$OZn, 658.171; found: 658.168.

Example 55

Synthesis of 5-(3-methylphenoxy)-10,20-diphenylporphinato zinc(II)

The general procedure was used to couple 5-bromo-10,20-diphenylporphinato zinc(II) (30 mg, 0.05 mmol) with 3-cresol (20 PL, 0.018 mmol), using palladium DBA (1.5 mg, 0.0075 mmol) as the palladium precursor, DPEphos (9.6 mg, 0.036 mmol) as the phosphine ligand and cesium carbonate (34 mg, 0.1 mmol) as the base. The reaction was conducted in toluene (5 mL) at 100° C. for 16 hours. Isolated via flash chromatography (silica gel, THF:hexanes (v)=1:8 as a red solid (25 mg, 78%). $^1$H NMR (300 MHz, CDCl$_3$): δ 10.03 (s, 1H), 9.36 (d, J=4.5 Hz, 2H), 9.25 (d, J=4.5 Hz, 2H), 9.00 (d, J=4.2 Hz, 2H), 8.89 (d, J=4.5 Hz, 2H), 8.2 (m, 4H), 7.76 (m, 6H), 7.10 (t, J=7.5 Hz, 1H), 6.80 (m, 3H), 2.15 (S, 3H). $^{13}$C NMR (75 MHz, CDCl$_3$): δ 166.1, 150.0, 150.2, 149.6, 145.8, 142.7, 139.7, 134.6, 132.7, 132.0, 131.6, 129.3, 127.9, 127.4, 126.5, 122.2, 120.3, 117.3, 113.7, 105.2, 21.4. UV-vis (CHCl$_3$, λ$_{max}$, nm): 418, 546. IR (film, cm$^{-1}$): 3053, 3024, 2922, 2877, 1587, 1542, 1484, 1458, 1440, 1384, 1360, 1321, 1294, 1248, 1217, 1188, 1158, 1061, 1039, 995, 911, 881, 848, 793, 781, 752, 723, 700. HRMS-EI ([M]$^+$): C$_{39}$H$_{26}$N$_4$OZn, 630.140; found: 630.139.

Example 56

Synthesis of 5-(4-methylphenoxy)-10,20-diphenylporphinato zinc(II)

The general procedure was used to couple 5-bromo-10,20-diphenylporphinato zinc(II) (30 mg, 0.05 mmol) with 4-cresol (20 mg, 0.018 mmol), using palladium acetate (1 mg, 0.005 mmol) as the palladium precursor, DPEphos (4.0 mg, 0.015 mmol) as the phosphine ligand and cesium carbonate (24 mg, 0.07 mmol) as the base. The reaction was conducted in toluene (5 mL) at 100° C. for 16 hours. Isolated via flash chromatography (silica gel, toluene:hexanes (v)= 3:1 as a red solid (21 mg, 65%). $^1$H NMR (300 MHz, CDCl$_3$): δ 9.97 (s, 1H), 9.30 (d, J=4.5 Hz, 2H), 9.21 (d, J=4.5 Hz, 2H), 8.92 (d, J=4.5 Hz, 2H), 8.8 (d, J=4.5 Hz, 2H), 8.13 (m, 4H), 8.13 (m, 6H), 6.97 (d, J=9.0 Hz, 2H), 6.86 (d, J=8.7 Hz, 2H), 2.2 (S, 3H). $^{13}$C NMR (75 MHz, CDCl$_3$): δ 150.3, 145.8, 143.4, 142.7, 134.6, 132.7, 132.0, 131.6, 130.4, 130.0, 128.9, 128.4, 127.9, 127.4, 126.5, 125.2, 120.3, 116.3, 105.2, 24.9. UV-vis (CHCl$_3$, λ$_{max}$, nm): 416, 546. IR (film, cm$^{-1}$): 3324, 2988, 1557, 1505, 1453, 1440, 1384, 1358, 1321, 1294, 1215, 1167, 1145, 1060, 993, 846, 820, 793, 753, 723. HRMS-EI ([M]$^+$): C$_{39}$H$_{26}$N$_4$OZn, 630.140; found: 630.141.

Example 57

Synthesis of 5-(2-methylphenoxy)-10,20-diphenylporphinato zinc(II)

The general procedure was used to couple 5-bromo-10,20-diphenylporphinato zinc(II) (30 mg, 0.05 mmol) with 2-cresol (20 mg, 0.018 mmol), using palladium DBA (1.5 mg, 0.0075 mmol) as the palladium precursor, DPEphos (9.6 mg, 0.036 mmol) as the phosphine ligand and cesium carbonate (24 mg, 0.07 mmol) as the base. The reaction was conducted in toluene (5 mL) at 100° C. for 17 hours. Isolated via flash chromatography (silica gel, toluene:hexanes (v)= 3:1 as a red solid (27.8 mg, 89%). $^1$H NMR (300 MHz, CDCl$_3$): δ 9.94 (s, 1H), 9.33 (d, J=4.8 Hz, 2H), 9.19 (d, J=4.5 Hz, 2H), 8.97 (d, J=4.2 Hz, 2H), 8.90 (d, J=4.8 Hz, 2H), 8.18 (m, 4H), 7.74 (m, 6H), 7.47 (d, J=6.9 Hz, 1H), 6.90 (t, J=7.2 Hz, 7.5 Hz 1H), 6.68 (t, J=7.5 Hz, 7.2 Hz 1H), 6.02 (d, J=8.4 Hz, 1H), 3.10 (S, 3H). $^{13}$C NMR (75 MHz, CDCl$_3$): δ 150.1, 149.9, 149.6, 145.7, 142.3, 140.7, 140.6, 140.6, 140.5, 134.5, 132.8, 132.1, 131.6, 131.0, 127.8, 127.5, 126.8, 126.6, 121.1, 116.2, 105.3, 17.0. UV-vis (CHCl$_3$, λ$_{max}$, nm): 415, 546. IR (film, cm$^{-1}$): 3047, 3024, 2922, 2877, 1587, 1542, 1484, 1458, 1440, 1384, 1359, 1321, 1294, 1217, 1188, 1158, 1061, 991, 908, 877, 851, 793, 779, 751, 723. HRMS-EI ([M]$^+$): C$_{39}$H$_{26}$N$_4$OZn, 630.140; found: 630.139.

Example 58

Synthesis of bis-5,15-(4-methoxyphenoxy)-10,20-diphenylporphinato zinc(II)

The general procedure was used to couple 5,15-dibromo-10,20-diphenylporphinato zinc(II) (34 mg, 0.05 mmol) with 4-methoxyphenol (22 mg, 0.018 mmol), using palladium DBA (1.5 mg, 0.0075 mmol) as the palladium precursor, DPEphos (9.6 mg, 0.036 mmol) as the phosphine ligand and cesium carbonate (47 mg, 0.14 mmol) as the base. The reaction was conducted in toluene (5 mL) at 100° C. for 18 hours. Isolated via flash chromatography (silica gel, THF:hexanes (v)=1:8 as a purple solid (26 mg, 68%). $^1$H NMR (300 MHz, THF-d$_8$): δ 9.28 (m, 4H), 8.77 (m, 4H), 8.17 (m, 4H), 7.73 (m, 6H), 8.8 (d, J=4.5 Hz, 2H), 8.13 (m, 4H), 7.73 (m, 6H), 6.95 (d, J=9.3 Hz, 4H), 6.77 (d, J=9.6 Hz, 4H), 3.67 (s, 6H). $^{13}$C NMR (75 MHz, CDCl$_3$): δ 155.4, 150.4, 147.8, 144.0, 135.3, 132.7, 128.4, 128.2, 127.2, 117.8, 115.3, 55.7. UV-vis (CHCl$_3$, λ$_{max}$, nm): 426, 554. IR (film, cm$^{-1}$): 3056, 2950, 2903, 2833, 2353, 1812, 1722, 1596, 1502, 1490, 1461, 1439, 1332, 1302, 1243, 1198, 1166, 1144, 1103, 1063, 1035, 1003, 920, 884, 827, 796, 751, 735, 722, 702. HRMS-EI ([M]$^+$): $C_{46}H_{32}N_4O_4Zn$, 768.162; found: 768.164.

It will be understood that various details of the invention may be changed without departing from the scope of the invention. Furthermore, the foregoing description is for the purpose of illustration only, and not for the purpose of limitation.

What is claimed is:

1. A porphyrin compound having the structure of Formula (I):

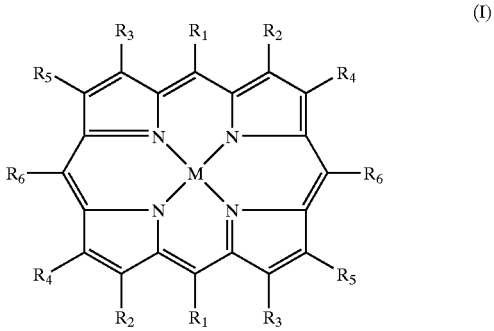

wherein:
M is $H_2$ or a transition metal;
each $R_1$, $R_2$, $R_3$, $R_4$, $R_5$ and $R_6$ are each independently selected from the group consisting of Y, H, alkyl, substituted alkyl, arylalkyl, aryl, and substituted aryl;
Y is a heteroatom-containing moiety selected from the group consisting of $NR_7R_8$, $NR_{10}$, $OR_{10}$, $PR_7R_8$, $SR_{10}$, $SiR_7R_8R_9$, $BR_7R_8$, $GeR_7R_8R_9$, $SnR_7R_8R_9$ and $SeR_{10}$, wherein:
  $R_7$ and $R_9$ are each independently selected from the group consisting of H, alkyl, substituted alkyl, arylalkyl, aryl, and substituted aryl;
  $R_8$ is selected from the group consisting of alkyl, arylalkyl, aryl, substituted aryl, and substituted alkyl, wherein the alkyl group substituent is selected from the group consisting of alkyl, halo, arylamino, acyl, hydroxy, aryloxy, alkoxyl, alkylthio, arylthio, aralkyloxy, aralkylthio, carboxy, oxo, and cycloalkyl;
  $R_{10}$ is selected from the group consisting of $C_2$–$C_{20}$ alkyl, aryl, substituted aryl, and substituted alkyl, wherein the alkyl group substitutent is selected from the group consisting of alkyl, halo, arylamino, acyl, hydroxy, aryloxy, alkoxyl, alkylthio, arylthio, aralkyloxy, aralkylthio, and cycloalkyl; and at least one of $R_1$, $R_2$, $R_3$, $R_4$, $R_5$ and $R_6$ is Y.

2. The compound according to claim 1, wherein M is selected from the group consisting of $H_2$, Zn, Fe and Ni.

3. The compound according to claim 1, wherein M is $H_2$ or Zn.

4. The compound according to claim 1, wherein Y is a phenoxy moiety.

5. The compound according to claim 1, wherein Y has the structure $NR_7R_8$.

6. The compound according to claim 5, wherein $R_7$ is H and $R_8$ is selected from the group consisting of alkyl, aryl, and substituted aryl.

7. The compound according to claim 1, wherein at least one $R_2$ is Y.

8. The compound according to claim 1, wherein at least one $R_2$ is Y and at least one $R_3$ is Y.

9. The compound according to claim 1, wherein at least one $R_2$ is Y, at least one $R_3$ is Y, and at least one $R_4$ is Y.

10. The compound according to claim 1, wherein at least one at least one $R_2$ is Y, at least one $R_3$ is Y, at least one $R_4$ is Y, and at least one $R_5$ is Y.

11. The compound according to claim 1, wherein at least one $R_6$ is Y.

12. The compound according to claim 1, wherein at least one $R_1$ and at least $R_6$ is Y.

13. The compound according to claim 1, wherein at least one of $R_1$ and $R_6$ is aryl, and said aryl is bound to at least one heteroatom-containing moiety Y.

14. The compound according to claim 13, wherein the aryl bound to at least one heteroatom-containing moiety Y has the structure:

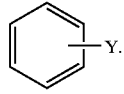

15. The compound according to claim 2, wherein at least one $R_6$ is Y, and wherein $R_7$ is H and $R_8$ is aryl.

16. The compound according to claim 2, wherein at least one $R_6$ is Y, and wherein $R_7$ is alkyl and $R_8$ is aryl.

17. The compound according to claim 2, wherein Y is $NR_{10}$ and $R_{10}$ has the structure:

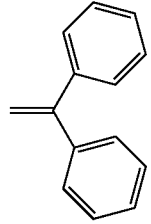

18. A method of synthesizing a heteroatom-substituted porphyrin compound, comprising reacting a porphyrin precursor with a reagent comprising a heteroatom, the porphyrin precursor having a structure of Formula I:

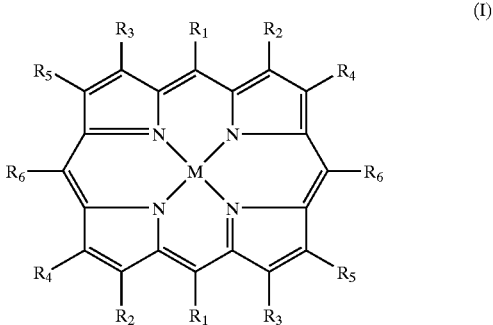

wherein
M is $H_2$ or a transition metal;
each $R_1$, $R_2$, $R_3$, $R_4$, $R_5$ and $R_6$ are each independently selected from the group consisting of X, H, alkyl, substituted alkyls, arylalkyls, aryls, and substituted aryls;
X is selected from the group consisting of halogen, trifluoromethanesulfonate (OTf), haloaryl and haloalkyl, and at least one of $R_1$, $R_2$, $R_3$, $R_4$, $R_5$ and $R_6$ is X;

wherein the reagent comprising a heteroatom has the structure H—Y and Y is a heteroatom-containing moiety
selected from the group consisting of $NR_7R_8$, $NR_{10}$, $OR_{10}$, $PR_7R_8$, $SR_{10}$, $SiR_7R_8R_9$, $BR_7R_8$, $GeR_7R_8R_9$, $SnR_7R_8R_9$ and $SeR_{10}$, wherein:
  $R_7$ and $R_9$ are each independently selected from the group consisting of H, alkyl, substituted alkyl, arylalkyl, aryl, and substituted aryl;
  $R_8$ is selected from the group consisting of alkyl, arylalkyl, aryl, substituted aryl, and substituted alkyl, wherein the alkyl grouo substituent is selected from the group consisting of alkyl, halo, arylamino, acyl, hydroxy, aryloxy, alkoxyl, alkylthio, arylthio, aralkyloxy, aralkylthio, carboxy, oxo, and cycloalkyl;
  $R_{10}$ is selected from the group consisting of $C_2$–$C_{20}$ alkyl, aryl, substituted aryl, and substituted alkyl, wherein the alkyl group substitutent is selected from the group consisting of alkyl, halo, arylamino, acyl, hydroxy, aryloxy, alkoxyl, alkylthio, arylthio, aralkyloxy, aralkylthio, and cycloalkyl; and
wherein the porphyrin precursor and reagent comprising a heteroatom are reacted in the presence of a metal compound, a ligand, and a base to produce a heteroatom-substituted porphyrin.

19. The method according to claim 18, wherein M is selected from the group consisting of $H_2$, Zn, Fe and Ni.

20. The method according to claim 18, wherein M is $H_2$ or Zn.

21. The method according to claim 18, wherein X is a halogen selected from the group consisting of Br, Cl, I and F.

22. The method according to claim 21, wherein X is Br.

23. The method according to claim 18, wherein at least one meso-position of the porphyrin precursor of Formula I is halogenated.

24. The method of claim 18, wherein the metal compound comprises a metal selected from the group consisting of Pd, Pt, Ni, or Cu.

25. The method according to claim 18, wherein the metal compound is a metal precursor compound selected from the group consisting of $Pd(dba)_2$, $Pd_2(dba)_3$, $Pd(OAc)_2$, $PdCl_2$, $Pd(TFA)_2$, and $(CH_3CN)_2PdCl_2$.

26. The method of claim 18, wherein the base is selected from the group consisting of n-BuLi, LDA, $NaNH_2$, NaOH, $Et_3N$, NaOAc, KOt-Bu, NaOt-Bu, $Cs_2CO_3$, $K_2CO_3$, and $K_3PO_4$.

27. The method according to claim 18, wherein Y has the structure $NR_7R_8$.

28. The method according to claim 18, wherein Y is selected from the group consisting of aniline, 4-nitroaniline, N-methylaniline, 4-trifluoromethylaniline, p-anisidine, 3,5-di-tert-butylaniline, n-hexylamine, benzylamine, diphenylamine, n-butylamine, 4-aminomethylpyridine, and o-toluidine.

29. The method according to claim 18, wherein Y is selected from the group consisting of phenol, 4-methoxyphenol, 4-t-butylphenol, 4-fluorophenol, 2-isopropylphenol, 3-cresol, 4-cresol, and 4-methoxyphenol.

30. The method according to claim 18, wherein the ligand is selected from the group of ligands consisting of:

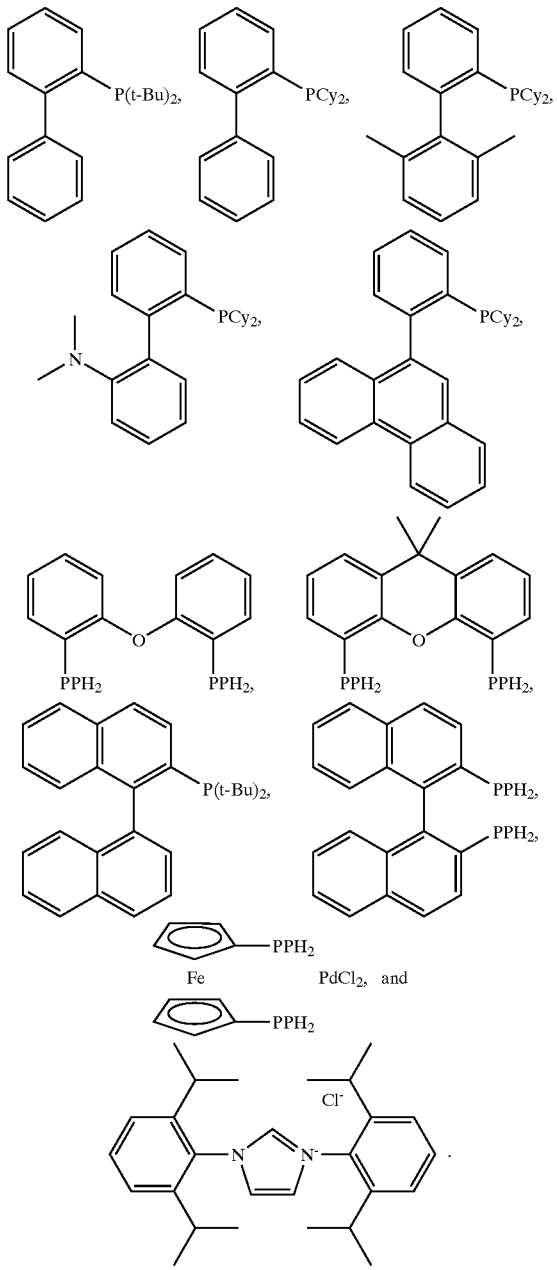

31. The method according to claim 18, wherein at least one $R_2$ is X.

32. The method according to claim 18, wherein at least one $R_2$ is X and at least one $R_3$ is X.

33. The method according to claim 18, wherein at least one $R_2$ is X, at least one $R_3$ is X, at least one $R_4$ is X.

34. The method according to claim 18, wherein at least one $R_2$ is X, at least one $R_3$ is X, at least one $R_4$ is X, and at least one $R_5$ is X.

35. The method according to claim 18, wherein at least one $R_6$ is X.

36. The method according to claim 18, wherein at least one $R_1$ and at least one $R_6$ is X.

* * * * *